United States Patent
Blaschuk et al.

(10) Patent No.: US 8,603,986 B2
(45) Date of Patent: Dec. 10, 2013

(54) COMPOUNDS AND METHODS FOR MODULATING CADHERIN-MEDIATED PROCESSES

(75) Inventors: Orest W. Blaschuk, Westmount (CA); Emmanuelle Marie-Madeleine Devemy, Montreal (CA)

(73) Assignee: McGill University, Montreal (CA)

( * ) Notice: Subject to any disclaimer, the term of this patent is extended or adjusted under 35 U.S.C. 154(b) by 771 days.

(21) Appl. No.: 11/912,857

(22) PCT Filed: Apr. 28, 2006

(86) PCT No.: PCT/US2006/016430
§ 371 (c)(1),
(2), (4) Date: Oct. 10, 2008

(87) PCT Pub. No.: WO2006/116737
PCT Pub. Date: Nov. 2, 2006

(65) Prior Publication Data
US 2010/0240066 A1    Sep. 23, 2010

Related U.S. Application Data

(60) Provisional application No. 60/676,091, filed on Apr. 28, 2005.

(51) Int. Cl.
*A61K 38/00* (2006.01)

(52) U.S. Cl.
USPC ........ 514/19.1; 514/21.5; 514/21.6; 530/327; 530/328

(58) Field of Classification Search
None
See application file for complete search history.

(56) References Cited

U.S. PATENT DOCUMENTS

| | | | |
|---|---|---|---|
| 6,277,824 B1 * | 8/2001 | Doherty et al. | 514/9.3 |
| 6,830,894 B1 | 12/2004 | Blaschuk et al. | |
| 2005/0222041 A1 * | 10/2005 | Biilmann et al. | 514/16 |

FOREIGN PATENT DOCUMENTS

| | | |
|---|---|---|
| WO | 2004/044000 A2 | 5/2004 |
| WO | 2004/048411 A2 | 6/2004 |

OTHER PUBLICATIONS

Database UniProt—XP002406775 (Nov. 20, 2003), Database accession No. ADA41037, the whole document.
International Search Report from corresponding PCT/US2006/016430.

* cited by examiner

*Primary Examiner* — Cecilia J Tsang
*Assistant Examiner* — Fred Reynolds
(74) *Attorney, Agent, or Firm* — Norton Rose Fulbright Canada LLP

(57) ABSTRACT

Peptides comprising a cadherin cell adhesion recognition (CAR) sequence, and compositions comprising such peptides, are provided. Methods of using such peptides for modulating cadherin-mediated processes in a variety of therapeutic contexts are also provided. Methods are also provided for identifying compounds that are capable of modulating cadherin-mediated processes.

11 Claims, No Drawings

SEQUENCE LISTING

```
<160> NUMBER OF SEQ ID NOS: 63

<210> SEQ ID NO 1
<211> LENGTH: 3
<212> TYPE: PRT
<213> ORGANISM: Unknown
<220> FEATURE:
<223> OTHER INFORMATION: Cell adhesion recognition sequence
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = Leu, Ile, Val, Phe, Met or Ala

<400> SEQUENCE: 1

Trp Xaa Xaa
 1

<210> SEQ ID NO 2
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 2

Trp Glu Phe Ser Ile Cys Glu Thr Cys
 1               5

<210> SEQ ID NO 3
<211> LENGTH: 9
<212> TYPE: PRT
<213> ORGANISM: Artificial Sequence
<220> FEATURE:
<223> OTHER INFORMATION: Cell adhesion recognition sequence
```

```
<400> SEQUENCE: 3

Trp Thr Val Cys Pro Ile Gly Asn Cys
 1               5

<210> SEQ ID NO 4
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 4

Trp Glu Val Cys Leu Thr Glu Lys Cys
 1               5

<210> SEQ ID NO 5
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 5

Trp Glu Leu Cys Val Ser Ser Ser Cys
 1               5

<210> SEQ ID NO 6
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 6

Trp Glu Val Arg Leu Thr Glu Lys Cys
 1               5

<210> SEQ ID NO 7
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 7

Trp Glu Leu Arg Val Ser Ser Pro Cys
 1               5

<210> SEQ ID NO 8
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 8

Trp Tyr Val Cys Val Gly Ala His Cys
 1               5

<210> SEQ ID NO 9
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 9
```

Trp Gln Val Cys Val Gly Ala His Cys
 1               5

<210> SEQ ID NO 10
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 10

Trp Thr Met Cys Tyr Pro Asp Thr Cys
 1               5

<210> SEQ ID NO 11
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 11

Trp Gln Phe Cys Tyr Ala Gln His Cys
 1               5

<210> SEQ ID NO 12
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 12

Trp Gln Met Val Leu Cys Pro Ala Cys
 1               5

<210> SEQ ID NO 13
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 13

Trp Glu Leu Val Gln Cys Leu Thr Cys
 1               5

<210> SEQ ID NO 14
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 14

Trp Thr Phe Asn Phe Cys Thr Ala Cys
 1               5

<210> SEQ ID NO 15
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 15

His Trp Tyr Ile Thr Thr Gly Pro Val Arg Glu Lys

<210> SEQ ID NO 16
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 16

Ser Trp Thr Leu Tyr Thr Pro Ser Gly Gln Ser Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 17

Asn Trp Phe Ile Asp Phe Pro Val Tyr Pro Pro Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 18

Lys Trp Glu Leu Thr Tyr Phe Ala Asn Ser Phe Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 19

Glu Trp Met Ile His Tyr Asp Ser Ala Leu Thr Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 20

Ala Trp Gln Val His Tyr Ser Tyr Val Ala Ser Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 21

Ser Trp Leu Ala Val Trp Pro Ala Thr Gly Ala Ser
1               5                   10

```
<210> SEQ ID NO 22
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 22

Ser Trp Thr Phe Tyr Trp Pro Asp Ala Gln Leu Gly
 1               5                  10

<210> SEQ ID NO 23
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 23

Glu Trp Thr Phe Gln Trp Asn Ser Tyr Pro Ala Asp
 1               5                  10

<210> SEQ ID NO 24
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 24

Glu Trp Asp Phe Phe Trp Pro Pro Thr Gln Thr Pro
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 25

Gln Trp Gln Leu His Trp Pro Ala Ser Lys Gln Ala
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 26

Gln Trp Thr Ile Thr Tyr Pro Lys Pro Pro Ala Leu
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 27

Gly Trp Thr Val Phe Tyr Pro Asp Asn Leu Arg Pro
 1               5                  10

<210> SEQ ID NO 28
```

```
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 28

Ser Trp Glu Leu Tyr Tyr Pro Leu Arg Ala Asn Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 29

Gln Trp Glu Ile Arg Tyr Pro Trp Pro Ser Met Gly
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Cell adhesion recognition sequence
<220> FEATURE:
<221> NAME/KEY: VARIANT
<222> LOCATION: 3
<223> OTHER INFORMATION: Xaa = Val, Leu or Phe
<220> FEATURE:
<221> NAME/KEY: VARIANT
<222> LOCATION: 4
<223> OTHER INFORMATION: Xaa = Cys, Ser or Arg
<220> FEATURE:
<221> NAME/KEY: VARIANT
<222> LOCATION: 5
<223> OTHER INFORMATION: Xaa = Val, Leu or Ile
<220> FEATURE:
<221> NAME/KEY: VARIANT
<222> LOCATION: 6
<223> OTHER INFORMATION: Xaa = Ser, Thr or Cys
<220> FEATURE:
<221> NAME/KEY: VARIANT
<222> LOCATION: 7
<223> OTHER INFORMATION: Xaa = Ser or Glu
<220> FEATURE:
<221> NAME/KEY: VARIANT
<222> LOCATION: 8
<223> OTHER INFORMATION: Xaa = Ser, Lys, Pro or Thr

<400> SEQUENCE: 30

Trp Glu Xaa Xaa Xaa Xaa Xaa Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: Cell adhesion recognition sequence
<220> FEATURE:
<221> NAME/KEY: VARIANT
<222> LOCATION: 2
<223> OTHER INFORMATION: Xaa = Leu or His
<220> FEATURE:
<221> NAME/KEY: VARIANT
<222> LOCATION: 3
<223> OTHER INFORMATION: Xaa = Gln or Thr
<220> FEATURE:
<221> NAME/KEY: VARIANT
<222> LOCATION: 4
<223> OTHER INFORMATION: Xaa = Pro or Ser
```

```
<220> FEATURE:
<221> NAME/KEY: VARIANT
<222> LOCATION: 5
<223> OTHER INFORMATION: Xaa = Tyr or Trp
<220> FEATURE:
<221> NAME/KEY: VARIANT
<222> LOCATION: 6
<223> OTHER INFORMATION: Xaa = Phe or Ser
<220> FEATURE:
<221> NAME/KEY: VARIANT
<222> LOCATION: 7
<223> OTHER INFORMATION: Xaa = Pro or Asp
<220> FEATURE:
<221> NAME/KEY: VARIANT
<222> LOCATION: 8
<223> OTHER INFORMATION: Xaa = Ser or Thr

<400> SEQUENCE: 31

Trp Xaa Xaa Xaa Xaa Xaa Xaa Xaa Tyr
 1               5

<210> SEQ ID NO 32
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 32

Trp Leu Gln Pro Tyr Phe Pro Ser Tyr
 1               5

<210> SEQ ID NO 33
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 33

Trp His Thr Ser Trp Ser Asp Thr Tyr
 1               5

<210> SEQ ID NO 34
<211> LENGTH: 8
<212> TYPE: PRT
<213> ORGANISM: Artificial Sequence
<220> FEATURE:
<223> OTHER INFORMATION: Cell adhesion recognition sequence
<220> FEATURE:
<221> NAME/KEY: VARIANT
<222> LOCATION: 2
<223> OTHER INFORMATION: Xaa = Tyr or Gln

<400> SEQUENCE: 34

Trp Xaa Val Cys Val Gly Ala His
 1               5

<210> SEQ ID NO 35
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 35

Trp Gln Trp Cys Phe Lys Ala Thr Cys
 1               5

<210> SEQ ID NO 36
```

```
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 36

Trp Thr Trp His Trp Pro Pro Cys Cys
1               5

<210> SEQ ID NO 37
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 37

Ser Trp Thr Trp His Phe Pro Glu Ser Pro Pro Pro
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 38

Glu Trp Thr Trp Val Phe Pro Thr Thr His Thr Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 39

Glu Trp Gln Tyr His Trp Pro Thr Leu Gln Ser Arg
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 40

Gln Trp Glu Trp His Tyr Met Ala Gly Tyr Leu Ala
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 41

Gln Trp Thr Tyr Tyr Leu Pro Leu Thr Pro Arg Trp
1               5                   10

<210> SEQ ID NO 42
<211> LENGTH: 12
<212> TYPE: PRT
```

-continued

```
<213> ORGANISM: Artificial Sequence
<220> FEATURE:
<223> OTHER INFORMATION: Cell adhesion recognition sequence

<400> SEQUENCE: 42

Glu Trp Thr Tyr Thr Phe Pro Thr Ala His Ser Ile
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 43

Glu Trp Phe Trp Ser Trp Pro Gly Tyr Ser Asn Thr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 44

Ser Trp Glu Trp Tyr Ile Pro Tyr Leu Asn Arg Thr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 45

Ala Trp Thr Trp Ser Leu Pro Thr Leu Pro Gln Ser
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Cell adhesion recognition sequence

<400> SEQUENCE: 46

Trp Tyr Val Cys Val Gly Ala His
1               5

<210> SEQ ID NO 47
<211> LENGTH: 8
<212> TYPE: PRT
<213> ORGANISM: Artificial Sequence
<220> FEATURE:
<223> OTHER INFORMATION: Cell adhesion recognition sequence

<400> SEQUENCE: 47

Trp Glu Leu Arg Val Ser Ser Pro
1               5

<210> SEQ ID NO 48
<211> LENGTH: 5
<212> TYPE: PRT
<213> ORGANISM: Artificial Sequence
<220> FEATURE:
```

```
<223> OTHER INFORMATION: Known cell adhesion recognition sequence that
      may be included with a modulating agent

<400> SEQUENCE: 48

Tyr Ile Gly Ser Arg
 1               5

<210> SEQ ID NO 49
<211> LENGTH: 10
<212> TYPE: PRT
<213> ORGANISM: Artificial Sequence
<220> FEATURE:
<223> OTHER INFORMATION: Known cell adhesion recognition sequence that
      may be included with a modulating agent

<400> SEQUENCE: 49

Lys Tyr Ser Phe Asn Tyr Asp Gly Ser Glu
 1               5                  10

<210> SEQ ID NO 50
<211> LENGTH: 17
<212> TYPE: PRT
<213> ORGANISM: Artificial Sequence
<220> FEATURE:
<223> OTHER INFORMATION: Known cell adhesion recognition sequence that
      may be included with a modulating agent

<400> SEQUENCE: 50

Ile Trp Lys His Lys Gly Arg Asp Val Ile Leu Lys Lys Asp Val Arg
 1               5                  10                  15

Phe

<210> SEQ ID NO 51
<211> LENGTH: 4
<212> TYPE: PRT
<213> ORGANISM: Artificial Sequence
<220> FEATURE:
<223> OTHER INFORMATION: Known cell adhesion recognition sequence that
      may be included with a modulating agent

<400> SEQUENCE: 51

Leu Tyr His Tyr
 1

<210> SEQ ID NO 52
<211> LENGTH: 8
<212> TYPE: PRT
<213> ORGANISM: Artificial Sequence
<220> FEATURE:
<223> OTHER INFORMATION: Known cell adhesion recognition sequence that
      may be included with a modulating agent
<220> FEATURE:
<221> NAME/KEY: VARIANT
<222> LOCATION: 2
<223> OTHER INFORMATION: Xaa = Lys or Arg
<220> FEATURE:
<221> NAME/KEY: VARIANT
<222> LOCATION: 3,4,7
<223> OTHER INFORMATION: Xaa = any amino acid
<220> FEATURE:
<221> NAME/KEY: VARIANT
<222> LOCATION: 5
<223> OTHER INFORMATION: Xaa = Ser or Ala
<220> FEATURE:
<221> NAME/KEY: VARIANT
<222> LOCATION: 6
<223> OTHER INFORMATION: Xaa = Tyr or Phe

<400> SEQUENCE: 52

Trp Xaa Xaa Xaa Xaa Xaa Xaa Gly
```

```
<210> SEQ ID NO 53
<211> LENGTH: 9
<212> TYPE: PRT
<213> ORGANISM: Artificial Sequence
<220> FEATURE:
<223> OTHER INFORMATION: Known cell adhesion recognition sequence that
      may be included with a modulating agent
<220> FEATURE:
<221> NAME/KEY: VARIANT
<222> LOCATION: 1, 3, 6, 7
<223> OTHER INFORMATION: Xaa = any amino acid
<220> FEATURE:
<221> NAME/KEY: VARIANT
<222> LOCATION: 4
<223> OTHER INFORMATION: Xaa = Ile, Leu or Val
<220> FEATURE:
<221> NAME/KEY: VARIANT
<222> LOCATION: 5
<223> OTHER INFORMATION: Xaa = Asp, Asn or Glu
<220> FEATURE:
<221> NAME/KEY: VARIANT
<222> LOCATION: 8
<223> OTHER INFORMATION: Xaa = Ser, Thr or Asn

<400> SEQUENCE: 53

Xaa Phe Xaa Xaa Xaa Xaa Xaa Xaa Gly
1               5

<210> SEQ ID NO 54
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 54

Ile Tyr Ser Tyr
1

<210> SEQ ID NO 55
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 55

Thr Ser Ser Tyr
1

<210> SEQ ID NO 56
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 56

Val Thr Ala Phe
1

<210> SEQ ID NO 57
<211> LENGTH: 4
<212> TYPE: PRT
<213> ORGANISM: Artificial Sequence
<220> FEATURE:
<223> OTHER INFORMATION: Representative claudin CAR sequence

<400> SEQUENCE: 57
```

```
Val Ser Ala Phe
 1

<210> SEQ ID NO 58
<211> LENGTH: 12
<212> TYPE: PRT
<213> ORGANISM: Artificial Sequence
<220> FEATURE:
<223> OTHER INFORMATION: Cell adhesion recognition sequence

<400> SEQUENCE: 58

Ser Arg Thr Leu Tyr Thr Pro Ser Gly Gln Ser Lys
 1               5                  10

<210> SEQ ID NO 59
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 59

Cys Ser Lys Tyr Asn Ser Pro Leu Cys
 1               5

<210> SEQ ID NO 60
<211> LENGTH: 9
<212> TYPE: PRT
<213> ORGANISM: Artificial Sequence
<220> FEATURE:
<223> OTHER INFORMATION: Cell adhesion recognition sequence

<400> SEQUENCE: 60

Cys Ser Arg Pro Gln Ser Gly Leu Cys
 1               5

<210> SEQ ID NO 61
<211> LENGTH: 8
<212> TYPE: PRT
<213> ORGANISM: Artificial Sequence
<220> FEATURE:
<223> OTHER INFORMATION: Cell adhesion recognition sequence

<400> SEQUENCE: 61

Ala Glu Leu Arg Val Ser Ser Pro
 1               5

<210> SEQ ID NO 62
<211> LENGTH: 8
<212> TYPE: PRT
<213> ORGANISM: Artificial Sequence
<220> FEATURE:
<223> OTHER INFORMATION: Cell adhesion recognition sequence

<400> SEQUENCE: 62

Arg Tyr Val Cys Val Gly Ala His
 1               5

<210> SEQ ID NO 63
<211> LENGTH: 12
<212> TYPE: PRT
```

-continued

```
<213> ORGANISM: Artificial Sequence
<220> FEATURE:
<223> OTHER INFORMATION: Cell adhesion recognition sequence PEGylated
<220> FEATURE:
<221> NAME/KEY: MOD_RES
<222> LOCATION: 12
<223> OTHER INFORMATION: succinyl-PEG5000-OMe

<400> SEQUENCE: 63

Ser Trp Thr Leu Tyr Thr Pro Ser Gly Gln Ser Lys
 1               5                  10
```

COMPOUNDS AND METHODS FOR MODULATING CADHERIN-MEDIATED PROCESSES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 640067_401USPCa_SEQUENCE_LISTING.txt. The text file is 16 KB, was created on May 11, 2010, and is being submitted electronically via EFS-Web.

TECHNICAL FIELD

The present invention relates generally to methods for modulating cadherin-mediated processes, and more particularly to the use of peptides for modulating cadherin-mediated processes. The present invention also relates to methods for identifying peptidyl and non-peptidyl compounds that are capable of modulating cadherin-mediated processes.

BACKGROUND OF THE INVENTION

Classical cadherins constitute a family of single-pass transmembrane glycoproteins that mediate calcium-dependent cell adhesion. Members of this family include E-cadherin, N-cadherin, R-cadherin, and P-cadherin. Cadherins promote cell adhesion in a homophilic manner (a cadherin on the surface of one cell binds to an identical cadherin on the surface of another cell) (Takeichi, (1990) *Ann. Rev. Biochem.*, 59, 237-252). Cadherins are not merely "biological glues". They are also capable of regulating different signaling pathways by virtue of their ability to interact with a variety of receptor protein kinases (such as the fibroblast growth factor receptor), as well as their ability to bind the intracellular signalling protein, known as β-catenin (Qian et al., (2004) *EMBO J.*, 23, 1739-1748).

The extracellular portion of classical cadherins is composed of five domains (EC1-EC5) of approximately 110 amino acids each separated by calcium binding sites. Calcium is absolutely required for the correct folding of the cadherin and confers a rod-like structure essential for adhesion with another cadherin molecule (Nagar et al., (1996) *Nature*, 380, 360-364). Cadherins are also composed of a single hydrophobic transmembrane domain and two cytoplasmic domains that link the cadherin molecule to different intracellular proteins such as β-catenin, γ-catenin and p120-catenin. These proteins in turn link cadherins to the cytoskeleton and other signaling molecules (Blaschuk et al., (2002) *Mol. Membr. Biol.*, 19, 75-80).

Inappropriate cadherin expression by specific cells is one of the mechanisms for cancer development, cell invasion and metastasis. E-cadherin is primarily expressed in epithelial cells and acts as a tumor suppressor. In carcinomas, E-cadherin expression is reduced or lost by genetic or epigenetic events (Van Aken et al., (2001) *Virchows Arch.*, 439, 725-751) and is accompanied by a loss of cell polarity and by cell dedifferentiation. Furthermore, transfection of carcinoma cells with E-cadherin cDNA results in a more differentiated and less invasive phenotype (Vleminckx et al., (1991) *Cell*, 66, 107-119). N-cadherin is expressed by many normal cell types including neural, vascular smooth muscle and endothelial cells, but not normal epithelial cells. N-cadherin is inappropriately expressed in many types of cancer. It has been reported that in carcinomas, loss of E-cadherin is accompanied by a de novo N-cadherin expression (Van Aken et al., (2001) *Virchows Arch.*, 439, 725-751). In cancer cells, N-cadherin plays an important role in tumor cell invasion and metastasis (Hazan et al., (2000) *J. Cell. Biol.*, 148, 779-790). In some cancer cells, E- and N-cadherin are coexpressed, but the contribution of N-cadherin to invasive potential takes precedence over E-cadherin function (Nieman et al., (1999) *J. Cell. Biol.*, 147, 631-644). In addition, tumor angiogenesis is essential for tumor development and metastasis (Folkman et al., (1992) *J. Biol. Chem.*, 267, 10931-10934) and targeting tumor vasculature represents a new approach to cancer treatment (Kelland, (2005) *Cur. Cancer Therapy Rev.*, 1, 1-9). N-cadherin is expressed by pericytes (smooth muscle-like cells) and endothelial cells, thereby ensuring the interactions of these cells, and therefore plays an essential role in blood vessel formation and the maintenance of blood vessel stability (Gerhardt et al., (2003) *Cell Tissue Res.*, 314, 15-23; Paik et al., (2004) *Genes Dev.*, 18, 2392-2403). N-cadherin antagonists have potential for selectively disrupting the tumor vasculature without effecting normal blood vessels. Such antagonists therefore represent promising anti-cancer drugs.

Permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells. Permeability barriers also make it difficult to deliver viruses (such as adenoviruses) to tissues (such as lungs), thus hampering gene therapy approaches to the treatment of diseases.

Attempts to facilitate the passage of drugs across such barriers generally rely on specific receptors or carrier proteins that transport molecules across barriers in vivo. However, such methods are often inefficient, due to low endogenous transport rates and/or to the poor functioning of a carrier protein when coupled with drugs. While improved efficiency has been achieved using a variety of chemical agents that disrupt cell adhesion, such agents are typically associated with undesirable side-effects, may require invasive procedures for administration and may result in irreversible effects.

Thus, there remains a need for agents capable of modulating one or more of the various processes mediated by classical cadherins, such as N-cadherin and E-cadherin. The present invention identifies, using phage display technology, new classes of peptide compositions effective for modulating classical cadherin-mediated processes, and offers other related advantages. The present invention also provides methods for identifying and using new compounds capable of modulating cadherin-mediated processes.

SUMMARY OF THE INVENTION

According to one aspect, the present invention provides a cell adhesion modulating agent that modulates a cadherin-mediated process and comprises a cell adhesion recognition (CAR) sequence having the following formula:

W-X-L/I/V/F/M/A     (SEQ ID NO: 1)

wherein X is an amino acid and wherein L/I/V/F/M/A is Leu or Ile or Val or Phe or Met or Ala.

In one embodiment according to this aspect of the invention, X comprises an amino acid selected from E, T, Y, Q, M, F, D, or L.

In another embodiment, the CAR sequence according to the above formula is selected from the group consisting of WEL, WTL, WYI, WEF, WQM, WEV, WTV, WYV, WQV, WTM, WQF, WTF, WMI, WDF, WTI, WFI, WQL, WEI, and WLA.

In a more particular embodiment, the CAR sequence is selected from the group consisting of WEFSICETC (SEQ ID NO: 2), WTVCPIGNC (SEQ ID NO: 3), WEVCLTEKC (SEQ ID NO: 4), WELCVSSSC (SEQ ID NO: 5), WEVRLTEKC (SEQ ID NO: 6), WELRVSSPC (SEQ ID NO: 7), WYVCVGAHC (SEQ ID NO: 8), WQVCVGAHC (SEQ ID NO: 9), WTMCYPDTC (SEQ ID NO: 10), WQFCYAQHC (SEQ ID NO: 11), WQMVLCPAC (SEQ ID NO: 12), WELVQCLTC (SEQ ID NO: 13), WTFNFCTAC (SEQ ID NO: 14), HWYITTGPVREK (SEQ ID NO: 15), SWTLYTPSGQSK (SEQ ID NO: 16), NWFIDFPVYPPL (SEQ ID NO: 17), KWELTYFANSFP (SEQ ID NO: 18), EWMIHYDSALTS (SEQ ID NO: 19), AWQVHYSYVASS (SEQ ID NO: 20), SWLAVWPATGAS (SEQ ID NO: 21), SWTFYWPDAQLG (SEQ ID NO: 22), EWTFQWNSYPAD (SEQ ID NO: 23), EWDFFWPPTQTP (SEQ ID NO: 24), QWQLHWPASKQA (SEQ ID NO: 25), QWTITYPKPPAL (SEQ ID NO: 26), GWTVFYPDNLRP (SEQ ID NO: 27), SWELYYPLRANL (SEQ ID NO: 28), and QWEIRYPWPSMG (SEQ ID NO: 29), or a portion thereof comprising at least an amino acid sequence selected from the group consisting of WEL, WTL, WYI, WEF, WQM, WEV, WTV, WYV, WQV, WTM, WQF, WTF, WMI, WDF, WTI, WFI, WQL, WEI, and WLA.

According to another aspect, the present invention provides a cell adhesion modulating agent that modulates a cadherin-mediated process and comprises a CAR sequence having the following formula:

W-E-V/L/F-C/S/R-V/L/I-S/T/C-S/E-S/K/P/T (SEQ ID NO: 30)

wherein V/L/F is Val or Leu or Phe, C/S/R is Cys or Ser or Arg, V/L/I is Val or Leu or Ile, S/T/C is Ser or Thr or Cys, S/E is Ser or Glu, S/K/P/T is Ser or Lys or Pro or Thr.

In a more particular embodiment of this aspect of the invention, the CAR sequence is selected from the group consisting of WEFSICETC (SEQ ID NO: 2), WEVCLTEKC (SEQ ID NO: 4), WELCVSSSC (SEQ ID NO: 5), WEVRLTEKC (SEQ ID NO: 6) and WELRVSSPC (SEQ ID NO: 7), or a portion thereof comprising at least an amino acid sequence selected from the group consisting of WEF, WEV and WEL.

In yet another aspect of the present invention, there is provided a cell adhesion modulating agent that modulates a cadherin-mediated process and comprises a CAR sequence having the following formula:

W-L/H-Q/T-P/S-Y/W-F/S-P/D-S/T-Y (SEQ ID NO: 31)

wherein L/H is Leu or His, Q/T is Gln or Thr, P/S is Pro or Ser, Y/W is Tyr or Trp, F/S is Phe or Ser, P/D is Pro or Asp, and S/T is Ser or Thr.

In a more particular embodiment of this aspect of the invention, the CAR sequence is selected from the group consisting of WLQPYFPSY (SEQ ID NO: 32) and WHTSWSDTY (SEQ ID NO: 33), or a portion thereof comprising at least an amino acid sequence selected from the group consisting of WLQ and WHT.

In another aspect of the present invention, there is provided a cell adhesion modulating agent that modulates a cadherin-mediated process and comprises a CAR sequence having the following formula:

```
W-Y/Q-VCVGAH        (SEQ ID NO: 34)
``` wherein Y/Q is Tyr or Gln.

In a more particular embodiment according to this aspect of the invention, there is provided a CAR sequence is selected from the group consisting of WYVCVGAHC (SEQ ID NO: 8) and WQVCVGAHC (SEQ ID NO: 9), or a portion thereof comprising at least an amino acid sequence selected from the group consisting of WYV and WQV.

According to another aspect of the invention, there is provided a cell adhesion modulating agent that modulates a cadherin-mediated process and comprises one or more CAR sequences selected from the group consisting of WTMCYPDTC (SEQ ID NO: 10), WQFCYAQHC (SEQ ID NO: 11), WQMVLCPAC (SEQ ID NO: 12), WELVQCLTC (SEQ ID NO: 13), WQWCFKATC (SEQ ID NO: 35), WTFNFCTAC (SEQ ID NO: 14), WTWHWPPCC (SEQ ID NO: 36), HWYITTGPVREK (SEQ ID NO: 15), SWTLYTPSGQSK (SEQ ID NO: 16), NWFIDFPVYPPL (SEQ ID NO: 17), KWELTYFANSFP (SEQ ID NO: 18), EWMIHYDSALTS (SEQ ID NO: 19), AWQVHYSYVASS (SEQ ID NO: 20), SWLAVWPATGAS (SEQ ID NO: 21), SWTWHFPESPPP (SEQ ID NO: 37), SWTFYWPDAQLG (SEQ ID NO: 22), EWTWVFPTTHTS (SEQ ID NO: 38), EWTFQWNSYPAD (SEQ ID NO: 23), EWDFFWPPTQTP (SEQ ID NO. 24), EWQYHWPTLQSR (SEQ ID NO: 39), QWQLHWPASKQA (SEQ ID NO: 25), QWTITYPKPPAL (SEQ ID NO: 26), GWTVFYPDNLRP (SEQ ID NO: 27), QWEWHYMAGYLA (SEQ ID NO: 40), SWELYYPLRANL (SEQ ID NO: 28), QWEIRYPWPSMG (SEQ ID NO: 29), QWTYYLPLTPRW (SEQ ID NO: 41), EWTYTFPTAHSI (SEQ ID NO: 42), EWFWSWPGYSNT (SEQ ID NO: 43), SWEWYIPYLNRT (SEQ ID NO: 44) and AWTWSLPTLPQS (SEQ ID NO: 45).

According to another aspect of the invention, there is provided a cell adhesion modulating agent that modulates a cadherin-mediated process and comprises one or more CAR sequences selected from the group consisting of WYVCVGAH (SEQ ID NO: 46), HWYITTGPVREK (SEQ ID NO: 15), SWTLYTPSGQSK (SEQ ID NO: 16), EWMIHYDSALTS (SEQ ID NO: 19), SWELYYPLRANL (SEQ ID NO: 28) and WELRVSSP (SEQ ID NO: 47).

According to another aspect, the invention provides a conservative analogue of a CAR sequence set forth above.

According to another aspect, the invention provides an antibody or antigen-binding fragment thereof that specifically binds to a CAR sequence set forth above.

According to another aspect, the invention provides a peptidomimetic of a CAR sequence set forth above.

In certain embodiments, the cell adhesion modulating agent is a peptide ranging in size from 3 to 50 amino acid residues, 3 to 25 amino acid residues or 3 to 10 amino acid residues.

The present invention further provides pharmaceutical compositions comprising a cell adhesion modulating agent as described above, in combination with a pharmaceutically acceptable carrier. Such compositions may further comprise a drug. Alternatively, or in addition, such compositions may comprise: (a) a peptide comprising a CAR sequence different than a CAR sequence identified according to the present invention and/or (b) an antibody or antigen-binding fragment thereof that specifically binds to a CAR sequence different than a CAR sequence of the invention.

Within further aspects, methods are provided for modulating cell adhesion, comprising contacting a cadherin-expressing cell with a cell adhesion modulating agent as described above.

Within further aspects, methods are provided for modulating cell proliferation, comprising contacting a cadherin-expressing cell with a cell adhesion modulating agent as described above.

Within further aspects, methods are provided for modulating cell migration, comprising contacting a cadherin-expressing cell with a cell adhesion modulating agent as described above.

Within further aspects, methods are provided for modulating cell survival, comprising contacting a cadherin-expressing cell with a cell adhesion modulating agent as described above. In certain embodiments, for example, cyclic peptides comprising dimers or multimers of a CAR sequence of the invention are provided for enhancing cell survival.

Within a further aspect, methods are provided for reducing unwanted cellular adhesion in a mammal, comprising contacting a cadherin-expressing cell with, or administering to a mammal, a cell adhesion modulating agent as described above, wherein the modulating agent inhibits cadherin-mediated cell adhesion.

In a further aspect, a method is provided for enhancing the delivery of a drug, e.g., to a tumor in a mammal, comprising contacting a cadherin-expressing cell with, or administering to a mammal, a cell adhesion modulating agent as described above and a drug, wherein the modulating agent inhibits cadherin-mediated cell adhesion.

In a related embodiment, the present invention also provides a method for enhancing the delivery of a drug through the skin of a mammal that comprises contacting epithelial cells of a mammal with a drug and a modulating agent that inhibits cadherin mediated cell adhesion and thereby enhancing the delivery of the drug through the skin. Also provided are kits for enhancing transdermal delivery comprising a skin patch and one or more modulating agents.

Within related aspects, methods for treating cancer and/or inhibiting metastasis of tumor cells in a mammal are provided, comprising contacting a cadherin expressing cell with, or administering to a mammal afflicted with cancer, a cell adhesion modulating agent as described above, wherein the modulating agent inhibits cadherin-mediated cell adhesion.

In a further aspect, methods are provided for inducing apoptosis in a cadherin-expressing cell, comprising contacting a cadherin-expressing cell with, or administering to a mammal, a cell adhesion modulating agent as described above, wherein the modulating agent inhibits cadherin-mediated cell adhesion.

In a further aspect, methods are provided for inhibiting apoptosis in a cadherin-expressing cell, comprising contacting a cadherin-expressing cell with, or administering to a mammal, a cell adhesion modulating agent as described above.

The present invention also provides, within other aspects, methods for inhibiting angiogenesis in a mammal, comprising contacting a cadherin-expressing cell with, or administering to a mammal, a cell adhesion modulating agent as described above, wherein the modulating agent inhibits cadherin-mediated cell adhesion.

The present invention also provides, within other aspects, methods for stimulating angiogenesis in a mammal, comprising contacting a cadherin-expressing cell with, or administering to a mammal, a cell adhesion modulating agent as described above, wherein the modulating agent enhances cadherin-mediated cell adhesion.

Methods are further provided, within other aspects, for stimulating blood vessel regression, comprising contacting a cadherin-expressing cell with, or administering to a mammal, a cell adhesion modulating agent as described above, wherein the modulating agent inhibits cadherin-mediated cell adhesion.

Within a further embodiment, the present invention provides methods for enhancing drug delivery to the central nervous system of a mammal, comprising contacting a cadherin-expressing cell with, or administering to a mammal, a cell adhesion modulating agent as described above, wherein the modulating agent inhibits cadherin-mediated cell adhesion.

In still further aspects, methods are provided for enhancing cell adhesion. Within one such aspect, for example, methods for enhancing wound healing in a mammal are provided, comprising contacting a wound in a mammal with a cell adhesion modulating agent as described above, wherein the modulating agent enhances cadherin-mediated cell adhesion.

Within a related aspect, the present invention provides methods for enhancing adhesion of foreign tissue implanted within a mammal, comprising contacting a site of implantation of foreign tissue in a mammal with a cell adhesion modulating agent as described above, wherein the modulating agent enhances cadherin-mediated cell adhesion.

In a further aspect, the present invention provides methods for treating a demyelinating neurological disease in a mammal, comprising contacting a cadherin-expressing cell with, or administering to a mammal, a cell adhesion modulating agent as described above, wherein the modulating agent inhibits cadherin-mediated cell adhesion.

Within a related aspect, the present invention provides methods for facilitating migration of a cadherin-expressing cell on astrocytes, comprising contacting a cadherin-expressing cell with (a) a cell adhesion modulating agent as described above and (b) one or more astrocytes; and thereby facilitating migration of the cadherin-expressing cell on the astrocytes.

The present invention also provides methods for modulating the immune system of a mammal, comprising administering to a mammal a cell adhesion modulating agent as described above, wherein the modulating agent inhibits cadherin-mediated cell adhesion.

In yet another aspect, methods for preventing pregnancy in a mammal are provided, comprising administering to a mammal a cell adhesion modulating agent as described above, wherein the modulating agent inhibits cadherin-mediated cell adhesion.

Within a further aspect, methods are provided for increasing vasopermeability in a mammal, comprising contacting a cadherin-expressing cell with, or administering to a mammal, a cell adhesion modulating agent as described above, wherein the modulating agent inhibits cadherin-mediated cell adhesion.

The present invention further provides methods for inhibiting synaptic stability in a mammal, comprising contacting a cadherin-expressing cell with, or administering to a mammal, a cell adhesion modulating agent as described above, wherein the modulating agent inhibits cadherin-mediated cell adhesion.

In other embodiments of the invention, there are provided methods for modulating the behavior, e.g., cell adhesion, proliferation, migration and/or survival, of vascular smooth muscle cells (VSMC) or pericytes, comprising contacting a cadherin-expressing VSMC or pericyte cell with, or administering to a mammal, a cell adhesion modulating agent as described above.

In a related embodiment, there are provided methods for regulating the overgrowth and/or migration of vascular smooth muscle cells or pericytes, comprising contacting a cadherin-expressing cell with, or administering to a mammal, a cell adhesion modulating agent as described herein, wherein the modulating agent is preferably an inhibitor of cadherin-mediated cell adhesion. Particularly illustrative uses according to this embodiment relate to preventing the formation or advance of restenosis, vein bypass graft failure, allograft vasculopathy, dialysis graft failure, thin cap fibroatheroma, and other vessel stenoses. Related embodiments include the treatment of essential and secondary hypertension, atheroma, arteriosclerosis, or other indications in which endothelial injury or trauma has occurred.

In another related embodiment, there are provided methods for maintaining vessel luminal area following vascular trauma, comprising contacting a cadherin-expressing cell with, or administering to a mammal, a cell adhesion modulating agent as provided herein, wherein the modulating agent is preferably an inhibitor of cadherin-mediated cell adhesion.

In another related embodiment, there are provided methods for treating a traumatized vessel, comprising contacting a cadherin-expressing cell with, or administering to a mammal, a cell adhesion modulating agent as provided herein, wherein the modulating agent is preferably an inhibitor of cadherin-mediated cell adhesion. Particularly illustrative uses according to this embodiment include the treatment of trauma that may occur during stent placement, organ transplant, vein bypass, angioplasty, dialysis graft placement, and the like.

In still other embodiments, one or more modulating agents are provided as an active component of a medical device (e.g. a balloon, stent, shunt, catheter, stent graft, vascular graft, vascular patch, filter, adventitial wrap, intraluminal paving system, cerebral stent, cerebral aneurysm filter coil, myocardical plug, pacemaker lead, dialysis access graft, heart valve, etc.). For example, the modulating agents of the invention may be linked to, coated on, or dispersed within essentially any medical device using known techniques in order to provide or deliver modulating agent in a desired physiological and/or anatomical context.

In these and other embodiments, the modulating agents of the present invention may be delivered to a cadherin-expressing cell, or a subject, by essentially any delivery approach suitable to a given indication and compatible with the delivery of modulating agents provided herein. In one embodiment, administration of a modulating agent provided herein is accomplished via a catheter. In another embodiment, administration of an agent is accomplished using an infusion needle.

There are also provided according to the invention methods for enhancing the survival of neurons and/or suppressing neural injury, for example as a result of stroke or other type of brain ischemia, comprising contacting a cadherin-expressing neural cell with, or administering to a mammal, a cell adhesion modulating agent as described above, wherein the modulating agent preferably is one that enhances cadherin-mediated cell adhesion.

Related embodiments of the invention are provided for treatment for stroke recovery, reversing or establishing plateau in dementias, treatment for trauma to the CNS, spine and peripheral nerves, as well as treatment of neuropathies.

In another embodiment, there are provided methods for enhancing neurite outgrowth comprising contacting a cadherin-expressing neural cell with, or administering to a mammal, a cell adhesion modulating agent as described above, wherein the modulating agent is preferably one that enhances cadherin-mediated cell adhesion.

In another embodiment, there are provided methods for facilitating the removal of hair follicles from skin, e.g., viable or intact hair follicles, comprising contacting a cadherin-expressing cell with, or administering to a mammal, a cell adhesion modulating agent of the invention. Certain aspects of this embodiment find particular utility in removing unwanted hair follicles and/or in the re-transplantation of hair follicles at a site of the body different from that in which they originated.

In other embodiments, methods are provided for stimulating angiogenesis comprising contacting a cadherin-expressing cell with, or administering to a mammal, a modulating agent provided herein, wherein the modulating agent enhances cadherin-mediated cell adhesion.

In still other embodiments, there are provided methods for modulating endothelial cell behavior, e.g., endothelial cell migration, proliferation, survival and/or adhesion comprising contacting a cadherin-expressing cell with, or administering to a mammal, a modulating agent provided herein.

Within further embodiments, methods are provided for modulating endothelial cell adhesion, comprising contacting a cadherin-expressing endothelial cell with, or administering to a mammal, a cell adhesion modulating agent as described herein. In certain preferred embodiments, the modulating agent inhibits cadherin mediated cell adhesion, resulting in the reduction of unwanted endothelial cell adhesion in the mammal.

Within further aspects, methods are provided for increasing vasopermeability in a mammal, comprising contacting a cadherin-expressing endothelial cell with, or administering to a mammal, a cell adhesion modulating agent as described above, wherein the modulating agent is preferably one that inhibits cadherin-mediated cell adhesion.

Methods are also provided, within further aspects, for disrupting neovasculature in a mammal, comprising contacting a cadherin-expressing cell with, or administering to a mammal, a modulating agent as described above, wherein the modulating agent inhibits cadherin-mediated cell adhesion.

Within further aspects, methods are provided for inhibiting the development of endometriosis in a mammal, comprising contacting a cadherin-expressing cell with, or administering to a mammal, a modulating agent as described above, wherein the agent is preferably one that inhibits cadherin-mediated cell adhesion.

In another embodiment, method are provided for modulating adipogenesis (a process dependent on angiogenesis) comprising contacting a cadherin-expressing cell with, or administering to a mammal, a modulating agent described herein, wherein the modulating agent is preferably one that inhibits cadherin-mediated cell adhesion.

In another embodiment, methods are provided for modulating tumor blood flow, comprising contacting a cadherin-expressing endothelial cell with, or administering to a mammal, a modulating agent described herein. Depending on the application, in certain embodiments, the modulating agent is preferably one that enhances cadherin-mediated cell adhesion while in others the modulating agent is preferably one that inhibits cadherin-mediated cell adhesion.

In still further embodiments, methods are provided for the treatment of disease conditions that are dependent on angiogenesis and neovascularization. Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofiboma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. These methods comprise contacting a cadherin-expressing cell with, or administering to a mammal, a modulating agent described herein, wherein the modulating agent preferably is one that inhibits cadherin-mediated cell adhesion.

In other embodiments, methods are provided for modulating FGF receptor activity. In one such embodiment, modulating agents that preferably inhibit cadherin-mediated cell adhesion are used for preventing the interaction between FGF receptor monomers. In another embodiment, modulating agents that enhance cadherin-mediated cell adhesion are preferably employed for their ability to promote the interaction between FGF receptor monomers.

In yet another embodiment, methods are provided for modulating tumor permeability barriers to drugs, such as chemotherapeutic agents, comprising contacting a cadherin-expressing cell with, or administering to a mammal, a modulating agent described herein.

In another embodiment, methods are provided for the modulation of bone adhesion, for example in the context of bone grafts, comprising contacting a cadherin-expressing cell with, or administering to a mammal, a modulating agent described herein, preferably a modulating agent that enhances cadherin-mediated cell adhesion. Modulating agents according to the invention may be effective, for example, in promoting bone adhesion to grafts. A single CAR-containing peptide attached to the solid support may serve as an agonist in this and other embodiments of the invention.

In another embodiment, there are provided methods for facilitating wound healing, comprising contacting a cadherin-expressing cell with, or administering to a mammal, a modulating agent described herein.

The present invention also provides a method for facilitating blood sampling in a mammal that comprises contacting epithelial cells of a mammal with a cell adhesion modulating agent that inhibits cadherin-mediated cell adhesion, thereby facilitating blood sampling in the mammal.

The present invention also provides a method for enhancing inhaled compound delivery in a mammal that comprising contacting lung epithelial cells of a mammal with a cell adhesion modulating agent that inhibits cadherin-mediated cell adhesion, thereby enhancing inhaled compound delivery.

The present invention also provides a method of ameliorating a spinal cord injury in a mammal that comprises administering to a mammal having a spinal cord injury a cell adhesion modulating agent that enhances cadherin-mediated cell adhesion, thereby ameliorating the spinal cord injury.

In another aspect, the present invention provides a method for screening a candidate compound for the ability to modulate a cadherin-mediated process that comprises comparing a three-dimensional structure of a candidate compound to a three-dimensional structure of a CAR sequence described herein, and evaluating the ability of the candidate compound to modulate a cadherin-mediated process. For such a method, the similarity between the structure of the candidate compound and the structure of the peptide may be indicative of the ability of the candidate compound to modulate a cadherin-mediated process.

According to another aspect of the invention, there is provided a method for identifying a cadherin antagonist that comprises: coating a well of a solid support, e.g. a plastic dish (or other polymeric support), with a chimeric protein such as an E-cadherin/Fc chimeric protein or an N-cadherin/Fc chimeric protein; contacting the chimeric protein with a phage display library, e.g. a peptide phage display library; removing non-specifically bound phage; eluting specifically bound phage; and sequencing the phage DNA to determine the peptide sequence.

According to another aspect of the invention, there is provided a method for identifying a compound (either an antagonist or agonist) capable of modulating cadherin-mediated processes that comprises: coating a well of a solid support, e.g. a plastic dish (or other polymeric support), with a chimeric protein such as a cadherin/Fc chimeric protein, wherein the chimeric protein can comprise any cadherin, including the classical cadherins P-cadherin and R-cadherin, as well as other types of cadherins, such as the nonclassical cadherins VE-cadherin and OB-cadherin; contacting the chimeric protein with a phage display library, e.g. a peptide phage display library; removing non-specifically bound phage; eluting specifically bound phage; and sequencing the phage DNA to determine the peptide sequence.

Another aspect of the invention provides a method for rapidly screening peptidyl or non-peptidyl libraries to identify E-cadherin and/or N-cadherin antagonists comprising: coating a solid support, e.g. a well of a plastic dish (or other polymeric support), with a chimeric protein such as an E-cadherin/Fc chimeric protein or an N-cadherin/Fc chimeric protein; contacting the chimeric protein with a phage that binds to the chimeric protein in the presence of a test compound; and determining if the test compound modulates binding of the phage to the chimeric protein for example by ELISA utilizing antibodies directed against the phage.

Another aspect of the invention provides a method for rapidly screening peptidyl or non-peptidyl libraries to identify compounds capable of modulating cadherin-mediated processes comprising: coating a solid support, e.g. a well of a plastic dish (or other polymeric support), with a chimieric protein such as a cadherin/Fc chimeric protein; contacting the chimeric protein with a phage that binds to the chimeric protein in the presence of a test compound; and determining if the test compound modulates binding of the phage to the chimeric protein for example by ELISA utilizing antibodies directed against the phage.

Another aspect of the invention provides a method for rapidly screening petidyl or non-peptidyl libraries to identify compounds capable of modulating cadherin-mediated processes comprising: coating a solid support, e.g. a well of a plastic dish (or other polymeric support), with the extracellular domain, or portion thereof of a cadherin; contacting the cadherin with phage that binds to the cadherin and determining if the binding of the phage to the cadherin protein is modulating in the presence of a test compound, for example by ELISA utilizing antibodies directed against the phage. The cadherin extracellular domain may, but need not be linked to another protein domain, such as the Fc domain of an immunoglobulin. The cadherin extracellular domain may, but need not be linked to another cadherin extracellular domain such that a dimer is formed. For example, for monomers, a cadherin protein comprising an extracellular domain or portion thereof may be covalently linked to a solid support or bead, for example via its N-terminus.

Another aspect of the invention provides a method for rapidly screening peptidyl or non-peptidyl libraries to identify classical cadherin antagonists, e.g., E-cadherin or N-cadherin antagonists, comprising: coating a solid support, e.g. a well of a plastic dish (or other polymeric support), with a chimeric protein such as a cadherin/Fc chimeric protein contacting the chimeric protein with a peptide containing a reporter group (such as an FITC labelled peptide) that binds to the chimeric protein; and determining if the binding of the labeled peptide to the chimeric protein is modulated in the presence of a test compound.

Another aspect of the invention provides a method for rapidly screening peptidyl or non-peptidyl libraries to identify compounds capable of modulating cadherin-mediated processes comprising: coating a solid support, e.g. a well of a plastic dish (or other polymeric support), with a chimeric protein such as a cadherin/Fc chimeric protein; contacting the chimeric protein with a peptide containing a reporter group (such as a peptide labeled with FITC) that binds to the chimeric protein; and determining if the binding of the labeled peptide to the chimeric protein is modulated in the presence of a test compound.

Another aspect of the invention provides a method for rapidly screening peptidyl or non-peptidyl libraries to identify compounds capable of modulating cadherin-mediated processes comprising: coating a solid support, e.g. a well of a plastic dish (or other polymeric support), with a chimeric protein such as a cadherin/Fc chimeric protein; contacting the chimeric protein with a phage that binds to the chimeric protein; and determining if the binding of the phage to the chimeric protein is modulated in the presence of the test compound, for example by ELISA utilizing antibodies directed against the phage.

These and other aspects of the invention will become evident upon reference to the following detailed description and attached drawings. All references disclosed herein are hereby incorporated by reference in their entirety as if each were individually noted for incorporation.

DETAILED DESCRIPTION OF THE INVENTION

The present invention employs phage display technology to identify new peptide sequences capable of modulating cadherin-mediated processes. The phage display system has been proven to facilitate the identification of compounds capable of binding specifically and with high affinity to their target. This technology was first described by George Smith in the mid-1980s (Smith, 1985). It allows repertoires of antibodies, proteins or peptides displayed on the surface of phage particles to be screened against any chosen target. Phage libraries are composed of millions of different permutations and are large enough to accommodate all possible combinations (Scott et al., (1990) *Science,* 249, 386-390). Peptide phage libraries have been used to identify small molecules that can bind to either purified targets or cell surface receptors (Landon et al., (2003) *J. Cell. Biochem.,* 90, 509-517).

The present invention provides cell adhesion modulating agents comprising one or more peptides comprising a cell adhesion recognition (CAR) sequence that is capable of modulating classical cadherin-mediated processes, such as cell adhesion, cell proliferation, cell migration and/or cell survival. Such modulating agents may generally be used, for example, to treat diseases or other conditions characterized by undesirable cell adhesion or to facilitate drug delivery to a specific tissue or tumor. Alternatively, certain modulating agents may be used to enhance cell adhesion (e.g., to supplement or replace stitches, or to facilitate wound healing or the attachment of implants) or to enhance or direct neurite outgrowth or to facilitate neuronal survival.

The term "CAR peptide" or "CAR sequence" as used herein, unless otherwise specified, refers to a peptide or salt thereof that comprises at least one classical CAR sequence identified according to the present invention. In addition to the CAR sequences of the invention, a modulating agent may comprise one or more additional known CAR sequences distinct from those defined according to the present invention, as further described herein, which may or may not be classical cadherin CAR sequences. The modulating agents of the invention may also comprise antibodies or fragments thereof that specifically recognize such known CAR sequences. These additional CAR sequences, or antibodies thereto, may be directly linked to a CAR sequence of the invention or may be represent a separate component of a modulating agent.

Within certain embodiments, a CAR sequence may comprise modified terminal groups, for example, an N-acetyl group (i.e., the amino group present on the amino terminal residue of the peptide is acetylated) or an N-formyl group (i.e., the amino group present on the amino terminal residue of the peptide is formylated), or the amino group present on the amino terminal residue of the peptide may be mesylated. It has been found, within the context of the present invention, that the presence of certain terminal groups may enhance peptide activity.

In certain related embodiments, the activity and/or stability of a modulating agent may be enhanced using one or more methodologies known and available in the art, for example by entrapment of a modulating agent within matrices or particles such as hydrogels, implants or nanoparticles, or by conjugation with other molecules such as polyethylene glycol and its derivatives. Polyethylene glycol (PEG) and its derivatives may be used as drug carriers given their high degree of biocompatibility. In addition, PEGylation provides beneficial effects on peptide pharmacokinetics and particularly can prolong the half-life of a peptide-based agent (e.g., Caliceti and Veronese M (2003), *Adv. Drug Deliv. Rev,* 55, 1261-1277).

The CAR sequences of the invention generally comprise from 3 to about 50 residues, from 3 to 25 residues or from 3-10 amino acid residues. Within certain embodiments, relatively small peptides that do not contain significant sequences flanking the CAR sequence are preferred for modulating N-cadherin and E-cadherin mediated cell adhesion. The finding, within certain embodiments of the present invention, that such relatively small peptides may be effective and all-purpose modulators of cadherin mediated processes, such as cell adhesion, represents a unexpected discovery. Such peptides can be thought of as "master keys" that fit into peptide binding sites of each of the different classical cadherins, and are capable of modulating cell adhesion of, for example, neural cells, endothelial cells, epithelial cells and/or certain cancer cells. Small peptides may generally be used to specifically modulate cell adhesion of neural and/or other cell types, e.g., by topical administration, systemic administration, and/or any other mode of administration appropriate for a given indication, with or without linking a targeting agent to the peptide, as discussed herein.

To facilitate the preparation of peptides having a desired specificity, nuclear magnetic resonance (NMR) and computational techniques may be used to determine the conformation of a peptide that confers a known specificity. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space and across the ring of the peptide. This information may be used to facilitate calculation of the low energy conformations for the CAR sequence. Conformation may then be correlated with tissue specificity to permit the identification of peptides that are similarly tissue specific or have enhanced tissue specificity.

Peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol. Modulating agents and peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

TABLE 1

Amino acid one-letter and three-letter abbreviations

| | | |
|---|---|---|
| A | Ala | Alanine |
| R | Arg | Arginine |
| D | Asp | Aspartic acid |
| N | Asn | Asparagine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |

Peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solid phase and solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthogonal systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

The structures and formulas recited herein are provided solely for the purpose of illustration, and are not intended to limit the scope of the peptides described herein.

Cell Adhesion Modulating Agents

The term "cell adhesion modulating agent," as used herein, refers to an agent that modulates one or more classical cadherin-mediated processes and comprises at least one peptide that contains a cadherin cell adhesion recognition (CAR) sequence, as identified herein, or an antibody or antigen-binding fragment thereof specific for a CAR sequence identified herein. As noted above, multiple CAR sequences may be present within a modulating agent. Further, additional CAR sequences known in the art, and different from those identified according to the present invention (i.e., any sequences specifically bound by an adhesion molecule) may be included within a modulating agent. As used herein, an "adhesion molecule" is any molecule that mediates cell adhesion via a receptor on the cell's surface. Adhesion molecules include, for example, members of the cadherin gene superfamily, such as desmogleins (Dsg) and desmocollins (Dsc); integrins; members of the immunoglobulin supergene family, such as N-CAM; and other transmembrane proteins, such as occludin and claudins, as well as extracellular matrix proteins such as laminin, fibronectin, collagens, vitronectin, entactin and tenascin.

Known CAR sequences that may be included within a modulating agent of the invention may include, for example, (a) RGD, which is bound by integrins (see Cardarelli et al., *J. Biol. Chem.* 267:23159-64, 1992); (b) YIGSR (SEQ ID NO: 48), which is bound by α6β1 integrin; (c) KYSFNYDGSE (SEQ ID NO: 49), which is bound by N-CAM; (d) the N-CAM heparin sulfate-binding site IWKHKGRD-VILKKDVRF (SEQ ID NO: 50); (e) the occludin CAR sequence LYHY (SEQ ID NO: 51); (f) claudin CAR sequences comprising at least four consecutive amino acids present within a claudin region that has the formula: Trp-Lys/Arg-Aaa-Baa-Ser/Ala-Tyr/Phe-Caa-Gly (SEQ ID NO: 52), wherein Aaa, Baa and Caa indicate independently selected amino acid residues; Lys/Arg is an amino acid that is lysine or arginine; Ser/Ala is an amino acid that is serine or alanine; and Tyr/Phe is an amino acid that is tyrosine or phenylalanine; and (g) nonclassical cadherin CAR sequences comprising at least three consecutive amino acids present within a nonclassical cadherin region that has the formula: Aaa-Phe-Baa-Ile/Leu/Val-Asp/Asn/Glu-Caa-Daa-Ser/Thr/Asn-Gly (SEQ ID NO: 53), wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. Representative claudin CAR sequences include IYSY (SEQ ID NO: 54), TSSY (SEQ ID NO: 55), VTAF (SEQ ID NO: 56) and VSAF (SEQ ID NO: 57). Representative nonclassical cadherin CAR sequences include the VE-cadherin (cadherin-5) CAR sequence DAE; the cadherin-6 CAR sequences EEY, NEN, ESE and DSG; the cadherin-7 CAR sequences DEN, EPK and DAN; the cadherin-8 CAR sequences EEF and NDV; the OB-cadherin (cadherin-11) CAR sequences DDK, EEY and EAQ; the cadherin-12 CAR sequences DET and DPK; the cadherin-14 CAR sequences DDT, DPK and DAN; the cadherin-15 CAR sequences DKF and DEL; the PB-cadherin CAR sequences EEY, DEL, DPK and DAD; the protocadherin CAR sequences DLV, NRD, DPK and DPS; the dsg CAR sequences NQK, NRN and NKD; the dsc CAR sequences EKD and ERD and the cadherin-related neuronal receptor CAR sequences DPV, DAD, DSV, DSN, DSS, DEK and NEK.

In certain preferred embodiments, a known CAR sequence included within a modulating agent of the invention comprises an N-cadherin CAR sequence, e.g., HAV, or a sequence comprising the HAV binding motif sequence such as INP (which is bound by classical cadherins). The above known CAR sequences and other related sequences are known and available to the skilled artisan and thus may be readily used in conjunction with the present invention.

Certain preferred known cadherin CAR sequences which may be used in the context of a modulating agent of the invention, or in a composition thereof, may comprise, for example, an HAV-containing CAR sequence as described in U.S. Pat. Nos. 6,031,072, 6,169,071, 6,207,639, 6,562,786, 6,346,512, 6,333,307, 6,417,325, 6,465,427, 6,610,821, 6,326,352, 6,780,845. Illustrative known HAV binding motif-containing sequences may include those described in U.S. Pat. Nos. 6,272,824, 6,472,368, 6,806,255. Illustrative known occludin CAR-containing sequences may include those described in U.S. Pat. Nos. 6,248,864, 6,110,747, 6,797,807, 6,310,177. Illustrative known non-classical cadherin CAR-containing sequences may include those described in U.S. Pat. Nos. 6,472,367, 6,358,920, 6,680,175, 6,593,297, 6,682,901, 6,433,149, 6,638,911, 6,569,996. Illustrative known claudin CAR-containing sequences may include those described in U.S. Pat. Nos. 6,756,356, 6,723, 700, 6,830,894. Illustrative known junctional adhesion molecule (JAM) CAR-containing sequences may include those described in U.S. Pat. No. 6,203,788. Antibodies specific for one or more such CAR sequences may also be used in the context of the modulating agents of the invention. Each of the above U.S. patents is specifically incorporated herein by reference.

Linkers may, but need not, be used to separate CAR sequences and/or antibody sequences within a modulating agent. Linkers may also, or alternatively, be used to attach one or more modulating agents to a support molecule or material, as described below. A linker may be any molecule (including peptide and/or non-peptide sequences as well as single amino acids or other molecules), that does not contain a CAR sequence and that can be covalently linked to at least two peptide sequences. Using a linker, CAR-containing peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise, for example, three different CAR sequences in addition to a CAR described herein, such as RGD, YIGSR (SEQ ID NO: 48) and HAV, one or more of which are present within a peptide. Within another embodiment, modulating agents having a branched structure comprise, for example, RGD, YIGSR (SEQ ID NO: 48), HAV and KYSFNYDGSE (SEQ ID NO: 49) in addition to a CAR described herein. In another illustrative embodiment, modulating agents comprising a CAR described herein may have a branched structure and may further comprise, for example, HAV and LYHY (SEQ ID NO: 51), along with one or more of NQK, NRN, NKD, EKD and ERD.

Linkers preferably produce a distance between CAR sequences between 0.1 to 10,000 nm, more preferably about 0.1-400 nm. A separation distance between recognition sites may generally be determined according to the desired function of the modulating agent. In certain embodiments, for inhibitors of cell adhesion, a small linker distance (e.g., 0.1-400 nm), may be desired. In certain other embodiments, for enhancers of cell adhesion, a longer linker distance (e.g., 400-10,000 nm) may be desired. However, these linker distances may vary substantially from one antagonist to another, and from one agonist to another, while still giving rise to a desired level of activity. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Modulating agents that inhibit cell adhesion may contain one or more CAR sequences, provided that such sequences are adjacent to one another (e.g. without intervening sequences) or in close proximity (e.g. separated by peptide and/or non-peptide linkers to give a distance between the CAR sequences that in some embodiments may range from about 0.1 to 400 nm). In other embodiments, the spacing between CAR motifs present within a CAR-containing multimer may vary while still giving rise to a desired level of inhibitory activity. Moreover, the degree of inhibitory activity of a given CAR-containing multimer may vary depending upon the concentration of the agent employed relative to the number of cadherin molecules being targeted in a given sample or subject, i.e., the level of saturation of the system being treated. Means for evaluating the antagonist activity of a CAR-containing multimer are provided elsewhere herein. It will be apparent that other CAR sequences, as discussed above, may also be included. Such modulating agents may generally be used within methods in which it is desirable to simultaneously disrupt cell adhesion mediated by multiple adhesion molecules. Within certain preferred embodiments, for example, an additional CAR sequence specific for a cell adhesion molecule other than a classical cadherin, for example a CAR from fibronectin recognized by an integrin (i.e., RGD; see Cardarelli et al., *J. Biol. Chem.* 267:23159-23164, 1992), or is derived from an occludin CAR sequence (e.g., LYHY; SEQ ID NO: 51). One or more antibodies, or fragments thereof, may similarly be used within such embodiments.

Modulating agents that enhance cell adhesion may also contain multiple CAR sequence motifs, provided such sequences are adjacent to one another in spatial orientation relative to one another that is effective for engaging two cadherin molecules, and thereby enhances cadherin-mediated adhesion and other cadherin-dependent processes. For example, dimeric forms of CAR-containing peptides may be useful in certain embodiments in which enhancement of N-cadherin-mediated processes is desired. Peptides comprising the sequence C-CAR-X-CAR-C, wherein X is 4-10 amino acids in length may be particularly preferred in certain embodiments. The spacing between CAR-containing motifs present within a CAR-containing multimer may vary while still giving rise to a desired level of agonist activity. A spacing of 1-10 amino acid residues, preferably 4-10 amino acid residues, between CAR-motifs in a CAR-containing multimer, for example, may be desirable in certain embodiments. Moreover, the degree of agonist activity of a given CAR-containing multimer may vary depending upon the concentration of the agent employed relative to the number of cadherin molecules being targeted in a given sample or subject, i.e., the level of saturation of the system being treated. Means for evaluating the agonist activity of a CAR-containing multimer are provided elsewhere herein. Enhancement of cell adhesion may also be achieved by attachment of a single CAR motif, multiple CAR-motifs and/or multiple modulating agents to a support molecule or material, as discussed further below. Such modulating agents may additionally comprise one or more CAR sequence for one or more different adhesion molecules (including, but not limited to, other CAMs) and/or one or more antibodies or fragments thereof that bind to such sequences, to enhance cell adhesion mediated by multiple adhesion molecules.

As noted above, a modulating agent may consist entirely of one or more peptides, or may contain additional peptide and/or non-peptide sequences. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode one or multiple CARs. To generate a nucleic acid molecule encoding a peptide portion of a modulating agent, a sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding a portion of the modulating agent.

As noted above, a modulating agent may also comprise an antibody, or antigen-binding fragment thereof, that specifically binds to a CAR sequence. As used herein, an antibody, or antigen-binding fragment thereof, is said to "specifically bind" to a CAR sequence (with or without flanking amino acids) if it reacts at a detectable level (within, for example, an ELISA, as described by Newton et al., *Develop. Dynamics* 197:1-13, 1993) with a peptide containing that sequence, and does not react detectably with peptides containing a different CAR sequence or a sequence in which the order of amino acid residues in the cadherin CAR sequence and/or flanking sequence is altered.

Antibodies and fragments thereof may be prepared using standard techniques. See, e.g., Harlow and Lane, *Antibodies: A Laboratory Manual*, Cold Spring Harbor Laboratory, 1988. In one such technique, an immunogen comprising a CAR sequence is initially injected into any of a wide variety of mammals (e.g., mice, rats, rabbits, sheep or goats). Small immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a CAR sequence may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction.

Antibody phage libraries (scFv, Fab libraries) can be constructed by known techniques, for example using large repertoires of single antibody fragment (scFv) or Fab antibody genes cloned into engineered phage or phagemid vectors, in a way that these antibody fragments are displayed on the surface of the phage. Immunoglobulin (Ig) variable region genes can derived from the B cells of a donor immunized with a protein or a peptide containing a CAR sequence (immune library) or from the B cells of a non-immunized donor (naïve library). The cloned genes can also be the result of a combination of germline V genes and synthetic oligonucleotide sequences encoding random CDRs (semi-synthetic library) or from fully synthetic sources (synthetic library). Immune and non-immune libraries are the most typically used libraries. They are prepared by extracting mRNA from B cells. The cDNA is synthesized using reverse transcriptase with chain specific primers (V genes) and used as a template for PCR amplification of antibody variable regions with primers complementary with the ends of the heavy- and light chain variable regions (Barbas III and al., Phage Display: A Laboratory Manual Cold Spring Harbor Laboratory, 2001). The heavy and light chain fragments can be converted by PCR to a single-chain Fv gene by inserting a DNA sequence coding for a flexible linker peptide. The PCR fragments are then inserted into a phage or phagemid vector DNA that is introduced into *E. Coli* by electroporation. These libraries are screened with immobilized cadherins or CAR containing peptides. The affinity of the isolated clones may be increased by chain shuffling. The Ig genes of the selected phage clones are introduced into an appropriate cell host that expresses the Ig in soluble form. Finally the Ig may be purified by affinity chromatography.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628-29).

Evaluation of Modulating Agent Activity

As noted above, peptides and other modulating agents as described herein are capable of modulating (i.e., enhancing or inhibiting) cadherin-mediated cell adhesion and/or other cadherin-dependent processes. The ability of a modulating agent to modulate cell adhesion may generally be evaluated in vitro, for example by assaying the effect on one or more of the following: (1) neurite outgrowth, (2) adhesion between endothelial cells, (3) adhesion between epithelial cells (e.g., normal rat kidney cells and/or human skin) and/or (4) adhesion between cancer cells (e.g. SKOV3 human ovarian cancer cells and/or MCF-7 human breast cancer cells). Other assays for the evaluation of cadherin-mediated function will be readily apparent in view of the disclosure herein. In general, a modulating agent is an inhibitor of cell adhesion if, within one or more of these representative assays, contact of the test cells with the modulating agent results in a discernible disruption of cell adhesion or other cadherin-mediated functions. Modulating agents that enhance cell adhesion are considered to be modulators of cell adhesion if they are capable of enhancing one or more cadherin-mediated functions, for example neurite outgrowth as described below and/or are capable of promoting cell adhesion, as judged by plating assays to assess epithelial cell adhesion to a modulating agent attached to a support material, such as tissue culture plastic. For modulating agents that affect N-cadherin mediated functions, assays involving endothelial or cancer cell adhesion or neurite outgrowth are preferred.

One illustrative screen for the ability to modulate classical cadherin-mediated cell adhesion may be performed by evaluating the ability of a modulating agent to bind to a classical cadherin using any binding assay known to those of ordinary skill in the art. For example, a Pharmacia Biosensor machine may be used, as discussed in Jonsson et al., *Biotechniques* 11:520-27, 1991. A specific example of a technology that measures the interaction of peptides with molecules can be found in Williams et al., *J. Biol. Chem.* 272, 22349-22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of the target molecule to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 g/ml) in 10 mM Sodium Acetate, pH 4.0, according to the manufacturer's protocol. Approximately 2100-2600 resonance units (RU) of ligand may be immobilized, corresponding to a concentration of about 2.1-2.6 ng/mm$^2$. The chips may then coated be with a classical cadherin (or portion thereof) derivatized to biotin. Any non-specifically bound protein is removed.

To determine binding, test analytes (e.g., peptides containing the CAR sequence) may be placed in running buffer and passed simultaneously over test and control flow cells. After a period of free buffer flow, any analyte (i.e. peptide) remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to a classical cadherin at a detectable level within such as assay. The level of binding is preferably at least that observed for the full length classical cadherin under similar conditions.

Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, Curr. Op. Neurobiol. 4:49-55, 1994; Williams et al., Neuron 13:583-594, 1994; Hall et al., Cell Adhesion and Commun. 3:441-450, 1996; Doherty and Walsh, Mol. Cell. Neurosci. 8:99-111, 1994; and Safell et al., Neuron 18:231-242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated neurite outgrowth may inhibit or enhance such neurite outgrowth. In at least some embodiments, under the conditions described above, the presence of 500 µg/mL of a modulating agent that disrupts neural cell adhesion should result in a decrease in the mean neurite length by at least 50%, relative to the length in the absence of modulating agent or in the presence of a negative control peptide. Alternatively, certain embodiments, the presence of 500 µg/mL of a modulating agent that enhances neural cell adhesion should result in an increase in the mean neurite length by at least 50%.

Within one representative cell adhesion assay, the addition of a modulating agent to cells that express a cadherin results in disruption of cell adhesion. A "cadherin-expressing cell," as used herein, may be any type of cell that expresses at least one cadherin, particularly N-cadherin and/or E-cadherin on the cell surface at a detectable level, using standard techniques such as immunocytochemical protocols (Blaschuk and Farookhi, Dev. Biol. 136:564-567, 1989). Cadherin-expressing cells include endothelial (e.g., bovine pulmonary artery endothelial cells), epithelial and/or cancer cells (e.g., the human ovarian cancer cell line SKOV3 (ATCC #HTB-77)). For example, such cells may be plated under standard conditions that permit cell adhesion in the presence and absence of modulating agent (e.g., 500 µg/mL). Disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/$cm^2$. Endothelial cultures may be used at 1 week in culture, which is approximately 3 days after culture confluency is established. The cells may be seeded onto coverslips and treated (e.g., for 30 minutes) with modulating agent or a control compound at, for example, 500 µg/ml and then fixed with 1% paraformaldehyde. As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC 4#1571-CRL) may be plated at 10-20,000 cells per 35 mm tissue culture flasks containing DMEM with 10% FCS and sub-cultured periodically (Laird et al., J. Cell Biol. 131:1193-1203, 1995). Cells may be harvested and replated in 35 mm tissue culture flasks containing 1 mm coverslips and incubated until 50-65% confluent (24-36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., J. Cell Biol. 131:1193-1203, 1995), of at least 75% within 48 hours.

Another cell adhesion assay involves evaluating the effect of a modulating agent on permeability of adherent epithelial and/or endothelial cell layers. For example, the effect on permeability of human skin may be evaluated. Such skin may be derived from a natural source or may be synthetic. Human abdominal skin for use in such assays may generally be obtained from humans at autopsy within 24 hours of death. Briefly, a peptide and a test marker (e.g., the fluorescent markers Oregon Green™ and Rhodamine Green™ Dextran) may be dissolved in a sterile buffer, and the ability of the marker to penetrate through the skin and into a receptor fluid may be measured using a Franz Cell apparatus (Franz, Curr. Prob. Dermatol. 7:58-68, 1978; Franz, J. Invest. Dermatol. 64:190-195, 1975). In general, a modulating agent that enhances the permeability of human skin results in a statistically significant increase in the amount of marker in the receptor compartment after 6-48 hours in the presence of 500 µg/mL modulating agent. This assay evaluates the effect of a modulating agent on E-cadherin mediated cell adhesion.

Yet another assay evaluates the effect of a modulating agent on the electrical resistance across a monolayer of cells. For example, Madin Darby canine kidney (MDCK) cells can be exposed to the modulating agent dissolved in medium (e.g., at a final concentration of 0.5 mg/ml for a period of 24 hours). The effect on electrical resistance can be measured using standard techniques. This assay evaluates the effect of a modulating agent on tight junction formation in epithelial cells. In general, the presence of 500 µg/mL modulating agent should result in a statistically significant decrease in electrical resistance after 24 hours.

Another cell adhesion assay evaluates the ability of a modulating agent to block angiogenesis (the growth of blood vessels from pre-existing blood vessels). This ability may be assayed using the chick chorioallantoic membrane assay described by Iruela-Arispe et al., *Molecular Biology of the Cell* 6:327-343, 1995. Briefly, a modulating agent may be embedded in a mesh composed of vitrogen at one or more concentrations (e.g., ranging from about 1 to 100 µg/mesh). The mesh(es) may then be applied to chick chorioallantoic membranes. After 24 hours, the effect of the peptide may be determined using computer assisted morphometric analysis. A modulating agent should inhibit angiogenesis by at least 25% at a concentration of 33 µg/mesh.

Alternatively, an agent may be evaluated in vivo by assessing the effect on vascular permeability utilizing the Miles assay (McClure et al., *J. Pharmacological & Toxicological Methods* 32:49-52, 1994). Briefly, a candidate modulating agent may be dissolved in phosphate buffered saline (PBS) at a concentration of 100 µg/ml. Adult rats may be given 100 µl subdermal injections of each peptide solution into their shaved backs, followed 15 minutes later by a single 250 µl injection of 1% Evans blue dissolved in PBS into their tail veins. The subdermal injection sites may be visually monitored for the appearance of blue dye. Once the dye appears (about 15 minutes after injection), each subdermal injection site may be excised, weighed, and placed in 1 ml dimethylformamide for 24 hours to extract the dye. The optical density of the dye extracts may then be determined at 620 nm. In general, the injection of 0.1 ml of modulating agent (at a concentration of 0.1 mg/ml) into the backs of rats causes an increase of dye accumulation at the injection sites of at least 50%, as compared to dye accumulation at sites into which PBS has been injected.

An illustrative assay for evaluating the ability of an agent to modulate vascular smooth muscle cell migration may be performed as follows (as described in Example 23). Human saphenous vein vascular smooth muscle cells are explanted from surplus segments of vein from patients undergoing coronary artery bypass surgery. Cells are maintained in Dulbecco's modified essential medium supplemented with penicillin, streptomycin, L-glutamine and 10% fetal calf serum and are grown to confluence on glass coverslips in the presence or absence of collagen type I. The cell layer is then subjected to scrape-wounding by drawing a fine cell scraper across the coverslip. Proliferation of the vascular smooth muscle cells is inhibited by addition of 2 mM hydroxyurea to the culture media. Vascular smooth muscle cells that are treated in this manner respond to the wounding of the confluent monolayer by migrating into the wound (Hammerle et al (1991) Vasa 20, 207-215). The migratory capacity of the vascular smooth muscle cells is assessed by measuring the distance of migration into the wound area (outermost 100 µm from the wound) using image analysis software at 24 hours after wounding.

Direct assays of induction of apoptosis may be performed using any standard technique. For example, cadherin-expressing cells (e.g., SKOV3 human ovarian cancer cells) may be plated onto poly-L-lysine coated glass slides and cultured with 500 µg/mL of modulating agent for 24-48 hours. Cells may then be fixed and assayed for cell death using any of a variety of well known methods. For example, an in situ cell death detection kit may be purchased from Boehringer Mannheim (Laval, Quebec) and used according to the manufacturer's instructions.

Modulating Agent Modification and Formulations

A modulating agent as described herein may, but need not, be linked to one or more additional molecules. In particular, as discussed herein, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain other embodiments, modulating agents may comprise one or more CAR sequences identified according to the present invention and may further comprise one or more known CAR sequences different from a CAR sequence of the invention (e.g., a known CAR sequence as described herein such as HAV, INP, RGD, LYHY (SEQ ID NO: 51), etc.) attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

For certain embodiments, a pharmaceutical composition may comprise one or more CAR sequences of the present invention, or antibodies thereto, and may further comprise one or more known CAR sequences capable of modulating cadherin and/or non-cadherin-mediated processes, or antibodies thereto. Such compositions may generally be prepared according to known methodologies and are particularly useful for situations in which it is desirable to inhibit cell adhesion mediated by multiple cell-adhesion molecules (including e.g., transmembrane proteins such as occluding, claudins, integrins, members of the immunoglobulin supergene family, such N-CAM; as well as extracellular matrix proteins such as laminin, fibronectin, collagens, vitronectin, entactin and tenascin), as well as other members of the cadherin gene superfamily that are either classical or non-classical adherins (including e.g., VE-cadherin; OB-cadherin, desmogleins; desmocollins). In certain embodiments, the known CAR sequences include those described herein, and preferably comprise the CAR sequences HAV, INP and related sequences.

A pharmaceutical composition may also contain one or more drugs, which may be linked to a modulating agent or may be free within the composition. Virtually any drug may be administered in combination with a peptide as described herein, for a variety of purposes as described below. Examples of types of drugs that may be administered with a peptide include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of peptide following administration). Such formulations may generally be prepared using well known technology and administered by, for example, oral, rectal or subcutaneous implantation, or by implantation at the desired target site. Sustained-release formulations may contain a peptide dispersed in a carrier matrix and/or contained within a reservoir surrounded by a rate controlling membrane (see, e.g., European Patent Application 710,491A). Carriers for use within such formulations are biocompatible, and may also be biodegradable; preferably the formulation provides a relatively constant level of peptide release. The amount of peptide contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10 μg to 2 mg/mL peptide. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of classical cadherin-expressing cells (i.e., cells that express one or more of E-cadherin, N-cadherin, P-cadherin, and/or R-cadherin in vitro and/or in vivo). To modulate classical cadherin-mediated cell adhesion, a cadherin-expressing cell is contacted with a modulating agent either in vivo or in vitro. As noted above, modulating agents for purposes that involve the disruption of cadherin-mediated cell adhesion may comprise a peptide containing a single CAR sequence as described herein or multiple CAR sequences in close proximity, and/or an antibody (or an antigen-binding fragment thereof) that recognizes a cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated by linkers. As noted above, such linkers may or may not comprise one or more amino acids. For enhancing cell adhesion, a modulating agent may contain multiple CAR sequences, as discussed above, or antibodies or antigen-binding fragments thereof, preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of cadherin-expressing cells.

As discussed in greater detail below, modulating agents as described herein may also be used to disrupt or enhance cell adhesion in a variety of other contexts. Within the methods described herein, one or more modulating agents may generally be administered alone, or within a pharmaceutical composition. In each specific method described herein, as noted above, a targeting agent may be employed to increase the local concentration of modulating agent at the target site.

In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function.

In addition, a modulating agent may comprise the sequence RGD, which is bound by integrins, and/or the sequence LYHY (SEQ ID NO: 51), which is bound by occludin, separated from the CAR sequence via a linker. Other known CAR sequences that may be present include OB-cadherin, desmoglein and desmocollin CAR sequences as described above. Alternatively, a separate modulator of integrin, occludin-, OB-cadherin-, desmocollin- and/or desmoglein-mediated cell adhesion may be administered in conjunction with the modulating agent(s), either within the same pharmaceutical composition or separately. Topical administration of the modulating agent(s) is generally preferred, but other means may also be employed. Preferably, a fluid composition for topical administration (comprising, for example, physiological saline) comprises an amount of peptide as described above, and more preferably an amount ranging from 10 μg/mL to 1 mg/mL. Creams may generally be formulated as described above. Topical administration in the surgical field may be given once at the end of surgery by irrigation of the wound, as an intermittent or continuous irrigation with use of surgical drains in the post operative period, or by the use of drains specifically inserted in an area of inflammation, injury or disease in cases where surgery does not need to be performed. Alternatively, parenteral or transcutaneous administration may be used to achieve similar results.

In another aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface.

Multifunctional modulating agents comprising one or more classical cadherin CAR sequences of the invention and further comprising one or more known CAR sequences as discussed above may also be used to disrupt epithelial cell adhesion. Certain illustrative known CAR sequences for use in this context include, for example, HAV CAR sequences, HAV binding motif sequences (e.g., INP, IDP etc), non-classical CAR sequences, desmocollin CAR sequences and/or the desmoglein CAR sequences. Such modulating agents may also, or alternatively, comprise the fibronectin CAR sequence RGD, which is recognized by integrins, the occludin CAR sequence LYHY (SEQ ID NO: 51) and/or a claudin CAR sequences as described above. Such known CAR sequence may be linked to a CAR sequence of the invention. Alternatively, a known CAR sequence may be present as a separate component which may be administered in conjunction with a modulating agent, either within the same pharmaceutical composition or separately. As noted above, these and related known CAR sequences are available in the art and can be readily used in conjunction with the modulating agents of the present invention.

Contact may be achieved by direct application of the modulating agent, generally within a composition formulated as a cream or gel, or using any of a variety of skin contact devices for transdermal application (such as those described in European Patent Application No. 566,816 A; U.S. Pat. No. 5,613,958; U.S. Pat. No. 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides a convenient measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g. every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and interferons may be delivered via the skin.

Kits for administering a drug via the skin of a mammal are also provided within the present invention. Such kits generally comprise a device for transdermal application (i.e., skin patch) in combination with, or impregnated with, one or more modulating agents. A drug may additionally be included within such kits.

Within a related embodiment, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt E-cadherin and/or N-cadherin mediated cell adhesion.

In one particularly preferred embodiment, a modulating agent is capable of disrupting cell adhesion mediated by multiple adhesion molecules. For example, a single branched modulating agent (or multiple agents linked to a single molecule or support material) may disrupt E-cadherin, N-cadherin, occludin, claudin, desmoglein and desmocollin mediated cell adhesion, thereby disrupting adherens junctions, tight junctions and desmosomes. Such an agent may comprise a cadherin CAR sequence, as well as one or more of the fibronectin CAR sequence RGD, which is recognized by integrins; a desmoglein CAR sequence; a desmocollin CAR sequence; a claudin CAR sequence; an occludin CAR sequence and/or an OB-cadherin CAR sequence. Such agents serve as multifunctional disrupters of cell adhesion. Alternatively, a separate modulator of non-classical cadherin-mediated cell adhesion may be administered in conjunction with the modulating agent(s), either within the same pharmaceutical composition or separately. Antibodies or Fab fragments directed against a cadherin CAR sequence and/or an occludin CAR sequence may also be employed, either incorporated into a modulating agent or within a separate modulator that is administered concurrently.

In a related embodiment, one or more CAR sequences of the invention are formulated with one or more drugs in the same composition or drug delivery device prior to administration. In general, a peptide may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the peptide and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of peptide administered varies with the method of administration and the nature of the tumor, within the typical ranges provided above, preferably ranging from about 1 µg/mL to about 2 mg/mL, and more preferably from about 10 µg/mL to 100 µg/mL. Transfer of the drug to the target tumor may be evaluated by appropriate means that will be apparent to those of ordinary skill in the art, such as a reduction in tumor size. Drugs may also be labeled (e.g., using radionuclides) to permit direct observation of transfer to the target tumor using standard imaging techniques.

Within a related aspect, the present invention provides methods for inhibiting the development of a cancer (i.e., for treating or preventing cancer and/or inhibiting metastasis) in a mammal. Cancer tumors are solid masses of cells, growing out of control, which require nourishment via blood vessels. The formation of new capillaries is a prerequisite for tumor growth and the emergence of metastases. Administration of a modulating agent as described herein may disrupt the growth of such blood vessels, thereby providing effective therapy for the cancer and/or inhibiting metastasis. Cancers that may be treated using modulating agents provided herein include any cancer in which the tumor cells or the supporting vasculature are dependent upon cadherin function, particularly N-cadherin function. Exemplary cancers treated according to this embodiment include cancers expressing N-cadherin, including, but not limited to, carcinomas, melanomas and leukemias. Preferably, a modulating agent prevents detectable tumor growth and/or results in a substantial decrease in tumor size (i.e., a reduction of at least 50%) and/or a substantial decrease in tumor cell proliferation, migration and/or survival according to assays known in the art and/or described herein.

Modulating agents comprising one or more CAR sequences of the invention may be used, for example, to treat leukemias. Preferred modulating agents for use within such methods include those that disrupt N-cadherin mediated cell adhesion. In addition, a modulating agent may comprise the sequence RGD, which is recognized by integrins, and/or the occludin CAR sequence LYHY (SEQ ID NO: 51) separated via a linker. Other CAR sequences that may be present include an OB-cadherin CAR sequence; desmocollin CAR sequence. desmoglein CAR sequence and/or claudin CAR sequence. Alternatively, a separate modulator of integrin-OB-cadherin-, desmocollin-, desmoglein-, claudin- and/or occludin-mediated cell adhesion may be administered in conjunction with the modulating agent(s), either within the same pharmaceutical composition or separately.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations such as the level of serum markers (e.g., CEA or PSA).

Within a further related aspect, a modulating agent may be used to inhibit angiogenesis (i.e., the growth of blood vessels from pre-existing blood vessels) in a mammal. In general, inhibition of angiogenesis may be beneficial in patients afflicted with diseases such as cancer or arthritis. In addition, a modulating agent for use in inhibiting angiogenesis may comprise the classical cadherin CAR sequence HAV, the classical cadherin HAV binding motif INP, the VE-cadherin CAR sequence DAE, the sequence RGD, which is recognized by integrins, the occludin CAR sequence LYHY (SEQ ID NO: 51) and/or a claudin CAR sequence, separated from the CAR sequence of the invention via a linker. Alternatively, a separate modulator of claudin-, VE-cadherin-, integrin- and/or occludin-mediated cell adhesion may be administered in conjunction with the modulating agent(s), either within the same pharmaceutical composition or separately.

The effect of a particular modulating agent on angiogenesis may generally be determined by evaluating the effect of the peptide on blood vessel formation. Such a determination may generally be performed, for example, using a chick chorioallantoic membrane assay (Iruela-Arispe et al., *Molecular Biology of the Cell* 6:327-343, 1995). Briefly, a modulating agent may be embedded in a mesh composed of vitrogen at one or more concentrations (e.g., ranging from about 1 to 100 μg/mesh). The mesh(es) may then be applied to chick chorioallantoic membranes. After 24 hours, the effect of the peptide may be determined using computer assisted morphometric analysis. A modulating agent should inhibit angiogenesis by at least 25% at a concentration of 33 μg/mesh.

The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Certain preferred modulating agents for use within such methods comprise, in addition to a CAR sequence of the invention, the classical cadherin CAR sequence HAV, the classical cadherin HAV binding motif INP, a nonclassical cadherin CAR sequence (preferably an OB-cadherin or VE-cadherin CAR sequence) a claudin CAR sequence, an occludin CAR sequence or the CAR sequence recognized by certain integrins RGD. Preferably, the peptide portion(s) of such modulating agents comprise 6-16 amino acids. Administration may be topical, via injection or by other means, and the addition of a targeting agent may be beneficial, particularly when the administration is systemic. Suitable modes of administration and dosages depend upon the location and nature of the endothelial cells and/or pericytes for which disruption of cell adhesion is desired but, in general, dosages may vary as described above. The addition of a targeting agent may be beneficial, particularly when the administration is systemic. Suitable modes of administration and dosages depend upon the condition to be prevented or treated but, in general, administration by injection is appropriate. Dosages may vary as described above.

In yet another related aspect, the present invention provides methods for inducing apoptosis in a cadherin-expressing cell. In general, patients afflicted with cancer may benefit from such treatment. Modulating agents comprising a CAR sequence for a second adhesion molecule (e.g., RGD, LYHY (SEQ ID NO: 51) or a CAR sequence for OB-cadherin, a desmoglein, a desmocollin or claudin) as well as the classical cadherin CAR sequence HAV and the HAV binding motif INP are also preferred. Alternatively, a separate modulator of cell adhesion mediated by an adhesion molecule that is not a cadherin may be administered in conjunction with the modulating agent(s), either within the same pharmaceutical composition or separately. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a peptide-drug-targeting agent combination, injection of a peptide (alone or in combination with a drug and/or targeting agent) into the carotid artery or application of a skin patch comprising a modulating agent to the head of the patient. Certain preferred peptides for use within such methods are relatively small (e.g., a ring size of 4-10 residues; preferably 5-7 residues). Also preferred are multi-functional modulating agents comprising the classical cadherin CAR sequence HAV, a VE-cadherin CAR sequence, an occludin CAR sequence LYHY (SEQ ID NO: 51) and/or claudin CAR sequence, preferably joined by a linker. Alternatively, a separate modulator classical cadherin (other than those recited herein) and/or VE-cadherin-, claudin, and occludin-mediated cell adhesion may be administered in conjunction with the modulating agent(s), either within the same pharmaceutical composition or separately. Fab fragments directed against an occludin CAR sequence may also be employed, either incorporated into the modulating agent or administered concurrently as a separate modulator.

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

In still further aspects, the present invention provides methods for enhancing adhesion of cadherin-expressing cells. Within certain embodiments, a modulating agent may be linked to a support molecule or to a solid support as described above, resulting in a matrix that comprises multiple modulating agents. Within one such embodiment, the support is a polymeric matrix to which modulating agents and molecules comprising other CAR sequence(s) are attached (e.g., modulating agents and molecules comprising HAV, INP, RGD, LYHY (SEQ ID NO: 51) or a CAR sequence for OB-cadherin, VE-cadherin, a desmoglein, a desmocollin or claudin, may be attached to the same matrix, preferably in an alternating pattern). Such matrices may be used in contexts in which it is desirable to enhance adhesion mediated by multiple cell adhesion molecules. Alternatively, the modulating agent itself may comprise multiple CAR sequences and/or antibodies (or fragments thereof), separated by linkers as described above. Either way, the modulating agent(s) function as a "biological glue" to bind multiple cadherin-expressing cells within a variety of contexts.

Within another embodiment, modulating agents may be used to enhance wound healing and/or reduce scar tissue in a mammal. In certain preferred embodiments, the modulating agent will comprise two or more CAR-containing motifs, properly spaced so as to provide a desired level of enhanced N-cadherin-mediated cell adhesion, migration and/or survival. Modulating agents that are linked to a biocompatible and biodegradable matrix such as cellulose or collagen are particularly preferred. For use within certain methods, a modulating agent should have a free amino or hydroxyl group. Multi-functional modulating agents further comprising the fibronectin CAR sequence RGD, which is recognized by integrins, as well CAR sequences for OB-cadherin, claudin, dsc and/or dsg, may also be used as potent stimulators of wound healing and/or to reduce scar tissue. Such agents may also, or alternatively, comprise the occludin CAR sequence LYHY (SEQ ID NO: 51). Alternatively, one or more separate modulators of classical cadherin (other than those recited herein), and/or integrin-, VE-cadherin, desmocollin-, desmoglein-, claudin-, OB-cadherin- and/or occludin-mediated cell adhesion may be administered in conjunction with the modulating agent(s), either within the same pharmaceutical composition or separately.

The modulating agents are generally administered topically to the wound, where they may facilitate closure of the wound and may augment, or even replace, stitches. Similarly, administration of matrix-linked modulating agents may facilitate cell adhesion in foreign tissue implants (e.g., skin grafting and prosthetic implants) and may prolong the duration and usefulness of collagen injection. In general, the amount of matrix-linked peptide administered to a wound, graft or implant site varies with the severity of the wound and/or the nature of the wound, graft, or implant, but may vary as discussed above.

Within another embodiment, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for larger scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of peptide(s) may also be used to facilitate the production of specific proteins.

Modulating agents as described herein may be used within a variety of bioreactor configurations. In general, a bioreactor is designed with an interior surface area sufficient to support larger numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Modulating agents may also be used, within other aspects of the present invention, to enhance and/or direct neurological growth. In one aspect, neurite outgrowth may be enhanced and/or directed by contacting a neuron with one or more modulating agents. Preferred modulating agents for use within such methods are linked to a polymeric matrix or other support and include those peptides without substantial flanking sequences, as described above. In certain preferred embodiments, the modulating agent will comprise two or more CAR-containing motifs, properly spaced so as to provide a desired level of enhanced cadherin-mediated cell adhesion, migration and/or survival. In addition, a modulating agent further comprising RGD and/or YIGSR (SEQ ID NO: 48), which are bound by integrins, and/or the N-CAM CAR sequence KYSFNYDGSE (SEQ ID NO: 49) may further facilitate neurite outgrowth. Other CAR sequences that may also, or alternatively, be included are CAR sequences for cadherin-7, cadherin-8, cadherin-12, cadherin-14, cadherin-15, PB-cadherin, protocadherins and cadherin-related neuronal receptors, as well as the CAR sequences HAV, INS and INP. Modulating agents comprising antibodies, or fragments thereof, may be used within this aspect of the present invention without the use of linkers or support materials. Fab fragments directed against the N-CAM CAR sequence KYSFNYDGSE (SEQ ID NO: 49) and/or the classical cadherin CAR sequence HAV may also be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another such aspect, one or more modulating agents may be used for therapy of a demyelinating neurological disease in a mammal. There are a number of demyelinating diseases, such as multiple sclerosis, characterized by oligodendrocyte death. It has been found, within the context of the present invention, that Schwann cell migration on astrocytes is inhibited by N-cadherin. Modulating agents that disrupt N-cadherin mediated cell adhesion as described herein may be implanted into the central nervous system with cells capable of replenishing an oligodendrocyte population, such as Schwann cells, oligodendrocytes or oligodendrocyte precursor cells. Such therapy may facilitate the cell capable of replenishing an oligodendrocyte population and permit the practice of Schwann cell or oligodendrocyte replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Preferred modulating agents for use within such methods include those that comprise one or more peptides provided herein. Modulating agents comprising antibodies, or fragments thereof, may also be used within this aspect of the present invention. Suitable amounts of peptide generally range as described above, preferably from about 10 µg/mL to about 1 mg/mL.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453-55, 1993; Baron-Van Evercooren et al., *Glia* 16:147-64, 1996). OPs can be isolated using routine techniques known in the art (see e.g., Milner and French-Constant, *Development* 120:3497-3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al, *J. Neurosci. Res.* 45:558-70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558-70, 1996).

An alternative source of OP may be spheres derived from CNS stem cells. Recently, Reynolds and Weiss, *Dev. Biol.* 165:1-13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1-13, 1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy. Neurosphere grafts may be implanted directly into the central nervous system along with the modulating agent(s) using standard techniques.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the peptide or pharmaceutical composition may be administered at a dosage ranging from 0.1 mg/kg to 20 mg/kg, although appropriate dosages may be determined by clinical trials. Methods of administration include injection, intravenous or intrathecal (i.e., directly in cerebrospinal fluid).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573-79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium- DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within a related aspect, the present invention provides methods for facilitating migration of an N-cadherin expressing cell on astrocytes, comprising contacting an N-cadherin expressing cell with (a) a cell adhesion modulating agent that inhibits cadherin-mediated cell adhesion, wherein the modulating agent comprises a CAR described herein; and (b) one or more astrocytes; and thereby facilitating migration of the N-cadherin expressing cell on the astrocytes. Preferred N-cadherin expressing cells include Schwann cells, oligodendrocytes and oligodendrocyte progenitor cells.

Within another aspect, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653-5659, 1994; Munro et al., *Cellular Immunol.* 169:309-312, 1996; Tsutsui et al., *J. Biochem.* 120:1034-1039, 1996; Cepek et al., *Proc. Natl. Acad. Sci. USA* 93:6567-6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-T cells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a peptide. Such treatment may also benefit patients undergoing transplantation with peripheral blood stem cells.

Within the above methods, the modulating agent(s) are preferably administered systemically (usually by injection) or topically. A peptide may be linked to a targeting agent. As noted above, a modulating agent may further be linked to a targeting agent. For example, targeting to the bone marrow may be beneficial. A suitable dosage is sufficient to effect a statistically significant reduction in the population of B and/ or T cells that express cadherin and/or an improvement in the clinical manifestation of the disease being treated. Typical dosages range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. In addition, a preferred modulating agent may comprise additional CAR sequences, such as the sequence RGD, which is bound by integrins and an OB-cadherin CAR sequence. As noted above, such additional sequences may be separated from the CAR sequence via a linker. Alternatively, a separate modulator of integrin-mediated cell adhesion may be administered in conjunction with the modulating agent(s), either within the same pharmaceutical composition or separately.

Suitable methods for incorporation into a contraceptive device depend upon the type of device and are well known in the art. Such devices facilitate administration of the peptide(s) to the uterine region and may provide a sustained release of the peptide(s). In general, peptide(s) may be administered via a contraceptive device at a dosage ranging from 0.1 to 20 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more peptides.

Alternatively, a sustained release formulation of one or more peptides may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein may be used to increase vascular permeability. Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. In addition, a preferred modulating agent may comprise an occludin CAR sequence LYHY (SEQ ID NO: 51) and/or a CAR sequence for VE-cadherin, OB-cadherin or claudin. As noted above, such an additional sequence may be separated from the CAR sequence of the invention via a linker. Alternatively, a separate modulator of occludin mediated cell adhesion may be administered in conjunction with one or modulating agents, either within the same pharmaceutical composition or separately.

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may comprise a CAR sequence which inhibits both N-cadherin and E-cadherin or may comprise a CAR sequence which will inhibit N-cadherin and a separate CAR sequence which inhibits E-cadherin.

In one particularly preferred embodiment, a modulating agent is further capable of disrupting cell adhesion mediated by multiple adhesion molecules. Such an agent may additionally comprise an RGD sequence, a desmocollin CAR sequence, a desmoglein CAR sequence, an OB-cadherin CAR sequence, a VE-cadherin, a claudin CAR sequence and/or the occludin CAR sequence LYHY (SEQ ID NO: 51). Alternatively, a separate modulator of non-classical cadherin-mediated cell adhesion may be administered in conjunction with the modulating agent(s), either within the same pharmaceutical composition or separately. Fab fragments directed against any of the above CAR sequences may also be employed, either incorporated into a modulating agent or within a separate modulator that is administered concurrently.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within a further aspect, modulating agents as described herein may be used for controlled inhibition of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty et al., *J. Neurobiology,* 26:437-446, 1995; Martin and Kandel, *Neuron,* 17:567-570, 1996; Fannon and Colman, *Neuron,* 17:423-434, 1996). Inhibition of cadherin function by administration of one or more modulating agents that inhibit cadherin function may stimulate learning and memory.

Preferred modulating agents for use within such methods include those that disrupt E-cadherin and/or N-cadherin mediated cell adhesion. In addition, a preferred modulating agent may comprise one or more non-classical cadherin CAR sequences, such as the sequence RGD, which is bound by integrins, the N-CAM CAR sequence KYSFNYDGSE (SEQ ID NO: 49) and/or a cadherin-related neuronal receptor CAR sequence. As noted above, such additional sequence(s) may be separated from the CAR sequence of the invention via a linker. Alternatively, a separate modulator of integrin, cadherin-related neuronal receptors and/or N-CAM mediated cell adhesion may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

In another embodiment, there are provided methods for facilitating wound healing, comprising contacting an cadherin-expressing cell with, or administering to a mammal, a modulating agent described herein. In certain diseases and disorders, for example, the body responds inappropriately to tissue damage, resulting in an excessive wound healing response. In the case of skin, this can result in formation of hypertrophic scars and keloids (Tredget E. E., Nedelec B., Scott P. G. and Ghahary A. Hypertrophic scars, keloids and contractures. Surgical Clinics of North America (1997) 77 (3) 701-730). A major factor in this dysfunctional wound-healing response is the activity of myofibroblast cells. Myofibroblasts are specialized cells with contractile properties of smooth muscle. Their appearance and contractility are essential for the healing of a wound (Tomasek J. J., Gabbiani G., Hinz B., Chaponnier C. and Brown R. A. Myofibroblasts and mechanoregulation of connective tissue remodelling. Nature Reviews Molecular Cell Biology (2002) 3 349-363; Singer A. J. and Clark R. A. F. Cutaneous wound healing. New England Journal of Medicine (1999) 341 (10) pp 738-746). They are formed by transformation from normally quiescent fibroblasts that are resident in the tissue surrounding the damage. Under normal circumstances myofibroblasts transform back to their quiescent state when wound healing is complete, but they may be retained as in a hypertrophic scar, or may transform even further toward a true smooth muscle cell phenotype. Cadherins may be important regulators of the transitions between these types of cells. Accordingly, modulating agents provided herein are used in certain embodiments for promoting wound healing or limiting excessive wound healing responses.

Within further aspects, the present invention provides methods for disrupting neovasculature (i.e., newly formed blood vessels). Such methods may be used to disrupt normal or pathological neovasculature in a variety of contexts. Disruption of neovasculature is therapeutic for conditions in which the presence of newly formed blood vessels is related to the underlying disorder, its symptoms or its complications. For example, disorders that may be treated include, but are not limited to, benign prostatic hyperplasia, diabetic retinopathy, vascular restenosis, arteriovenous malformations, meningioma, hemangioma, neovascular glaucoma, psoriasis, angiofibroma, arthritis, atherosclerotic plaques, corneal graft neovascularization, hemophilic joints, hypertrophic scars, hemorrhagic telangiectasia, pyogenic granuloma, retrolental fibroplasias, scleroderma trachoma, vascular adhesions, synovitis, dermatitis, endometriosis, macular degeneration and exudative macular degeneration. In addition, a preferred modulating agent may comprise the classical CAR sequence HAV and or the HAV biding motifs INP and INS, an occludin CAR sequence LYHY (SEQ ID NO: 51) and/or a CAR sequence for VE-cadherin, JAM or claudin, in addition to one or more CAR sequence identified according to the invention. As noted above, such an additional sequence may be separated from the CAR sequence of the invention via a linker. Alternatively, a separate modulator of classical cadherin-occludin-, VE-cadherin-, JAM and/or claudin-mediated cell adhesion may be administered in conjunction with one or of the modulating agents identified according to the invention, either within the same pharmaceutical composition or separately.

In other embodiments of the invention, there are provided methods for modulating the behavior, e.g., cell adhesion, proliferation, migration and/or survival, of vascular smooth muscle cells (VSMC) or pericytes, comprising contacting a cadherin-expressing cell with, or administering to a mammal, a cell adhesion modulating agent as described above.

As referred to herein, smooth muscle cells and pericytes include those cells derived from the medial layers of vessels and adventitia vessels which proliferate in intimal hyperplastic vascular sites following injury, such as that caused during PTCA.

Characteristics of smooth muscle cells include a histological morphology (under light microscopic examination) of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus. The majority of the sarcoplasm is occupied by thin, parallel myofilaments that may be, for the most part, oriented to the long axis of the muscle cell. These actin containing myofibrils may be arranged in bundles with mitochondria interspersed among them. Scattered through the contractile substance of the cell may also be oval dense areas, with similar dense areas distributed at intervals along the inner aspects of the plasmalemma.

Characteristics of pericytes include a histological morphology (under light microscopic examination) characterized by an irregular cell shape. Pericytes are found within the basement membrane that surrounds vascular endothelial cells and their identity may be confirmed by positive immunostaining with antibodies specific for alpha smooth muscle actin (e.g., anti-alpha-sm1, Biomakor, Rehovot, Israel), HMW-MAA, and pericyte ganglioside antigens such as MAb 3G5 (11); and, negative immuno-staining with antibodies to cytokeratins (i.e., epithelial and fibroblast markers) and Von Willebrand factor (i.e., an endothelial marker). Both vascular smooth muscle cells and pericytes are positive by immunostaining with the NR-AN-01 monoclonal antibody.

In related embodiments, there are provided methods for regulating the overgrowth and/or migration of vascular smooth muscle cells or pericytes, comprising contacting a cadherin-expressing cell with, or administering to a mammal, a cell adhesion modulating agent as described herein, wherein the modulating agent is preferably an inhibitor of cadherin-mediated cell adhesion. Particularly illustrative uses according to this embodiment relate to preventing the formation or advance of restenosis, vein bypass graft failure, allograft vasculopathy, dialysis graft failure, thin cap fibroatheroma, and other vessel stenoses.

The modulating agents of the invention are thus useful, for example, in inhibiting the activity of vascular smooth muscle cells, e.g., for reducing, delaying, or eliminating stenosis following angioplasty. As used herein the term "reducing" means decreasing the intimal thickening that results from stimulation of smooth muscle cell proliferation following angioplasty, either in an animal model or in man. "Delaying" means delaying the time until onset of visible intimal hyperplasia (e.g., observed histologically or by angiographic examination) following angioplasty and may also be accompanied by "reduced" restenosis. "Eliminating" restenosis following angioplasty means completely "reducing" and/or completely "delaying" intimal hyperplasia in a patient to an extent which makes it no longer necessary to surgically intervene, i.e., to re-establish a suitable blood flow through the vessel by repeat angioplasty, atheroectomy, or coronary artery bypass surgery. The effects of reducing, delaying, or eliminating stenosis may be determined by methods routine to those skilled in the art including, but not limited to, angiography, ultrasonic evaluation, fluoroscopic imaging, fiber optic endoscopic examination or biopsy and histology. The therapeutic conjugates of the invention achieve these advantageous effects by specifically binding to the cellular membranes of smooth muscle cells and pericytes.

In another embodiment, the modulating agents of the invention may be used in situations in which angioplasty is not sufficient to open a blocked artery, such as those situations which require the insertion of an intravascular stent. The stent, as well as other medical devices and implants described herein, preferably have linked or coated to the surface, or interspersed within, one or more modulating agents of the invention. In one embodiment of the invention, a metallic, plastic or biodegradable intravascular stent is coated with a biodegradable coating or with a porous non-biodegradable coating, having dispersed therein the sustained-release dosage form. In an alternative embodiment, a biodegradable stent may also have the therapeutic agent impregnated therein, i.e., in the stent matrix. Utilization of a biodegradable stent with the modulating agent impregnated therein which is further coated with a biodegradable coating or with a porous non-biodegradable coating having the sustained release-dosage form dispersed therein is also contemplated.

In another related embodiment, there are provided methods for maintaining vessel luminal area following vascular trauma, comprising contacting a cadherin-expressing cell with, or administering to a mammal, a cell adhesion modulating agent as provided herein, wherein the modulating agent is preferably an inhibitor of cadherin-mediated cell adhesion.

In another related embodiment, there are provided methods for treating a traumatized vessel, comprising contacting a cadherin expressing cell with, or administering to a mammal, a cell adhesion modulating agent as provided herein, wherein the modulating agent is preferably an inhibitor of cadherin-mediated cell adhesion. Particularly illustrative uses according to this embodiment include the treatment of trauma that may occur during stent placement, organ transplant, vein bypass, angioplasty, dialysis graft placement, and the like. Administration of the modulating agent may occur before, during or after the vascular trauma In these and other embodiments, the modulating agents of the present invention may delivered to a cadherin expressing cell, or a subject, by essentially any delivery approach suitable to a given indication and compatible with the delivery of modulating agents provided herein. In certain embodiments, administration of a modulating agent provided herein is accomplished via a catheter. In other embodiments, administration of an agent is accomplished using an infusion needle.

According to other aspects of the invention, modulating agents provided herein are linked to, coated upon, or dispersed within, for example, a solid support, such as a polymeric material or matrix. In one embodiment, the polymeric material is a biodegradable polymer suitable for in vivo implantation. In another embodiment, the polymeric material is a plastic. In another embodiment, the polymeric material is a microparticle or nanoparticle or a mixture thereof. Many such polymers, microparticles and nanoparticles have been described and can be selected and used for the controlled release and delivery of modulating agents of the invention using techniques well known and established in the art.

Certain embodiments will employ an implantable medical material or device, such as a medical device having a modulating agent of the invention linked to, or coated upon, or dispersed within, the medical material or device using known techniques. Such methods allow for the delivery of modulating agent, for example following implantation of the material or device into a mammal. Particularly illustrative medical devices in this regard include intravascular, intervascular and other medical devices, including a balloon, stent, shunt, catheter, stent graft, vascular graft, vascular patch, filter, adventitial wrap, intraluminal paving system, cerebral stent, cerebral aneurysm filter coil, myocardial plug, pacemaker lead, dialysis access graft, heart valve, etc.

Other aspects of the present invention provide methods that employ antibodies raised against the modulating agents for diagnostic and assay purposes. Such polyclonal and monoclonal antibodies may be raised against a peptide using conventional techniques known to those of ordinary skill in the art. See, e.g., Harlow and Lane, *Antibodies: A Laboratory Manual*, Cold Spring Harbor Laboratory, 1988. In one such technique, an immunogen comprising the peptide is initially injected into any of a wide variety of mammals (e.g., mice, rats, rabbits, sheep or goats). Because of its small size, the peptide should be joined to a carrier protein, such as bovine serum albumin or keyhole limpet hemocyanin. Following one or more injections, the animals are bled periodically. Polyclonal antibodies specific for the peptide may then be purified from such antisera by, for example, affinity chromatography using the polypeptide coupled to a suitable solid support.

Monoclonal antibodies specific for the peptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the immunogen. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Peptides may also be used to generate monoclonal antibodies, as described above, that are specific for particular cadherins (e.g., antibodies that bind to E-cadherin, but do not bind significantly to N-cadherin, or vise versa). Such antibodies may generally be used for therapeutic, diagnostic and assay purposes.

Assays typically involve using an antibody to detect the presence or absence of a cadherin (free or on the surface of a cell), or proteolytic fragment containing the EC1 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing the EC1 domain, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of a cadherin in a sample is a two-antibody sandwich assay. This assay may be performed by first contacting an antibody that has been immobilized on a solid support, commonly the well of a microtiter plate, with the biological sample, such that the cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups.

Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, peptides or antibodies thereto may be used to facilitate cell identification and sorting in vitro or imaging in vivo, permitting the selection of cells expressing different cadherins (or different cadherin levels). Preferably, the peptide(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a peptide or antibody linked to a fluorescent marker, such as fluorescein, is contacted with the cells, which are then analyzed by fluorescence activated cell sorting (FACS).

As noted above, in addition to diagnostic and assay purposes, antibodies as described herein may be used in vitro or in vivo to modulate cell adhesion. Within certain embodiments, antibodies may be used within methods in which enhanced cell adhesion is desired, as described above. For example, antibodies may be used within the above methods for enhancing and/or directing neurite outgrowth in vitro or in vivo. Antibodies may be used within the lumen of a tubular nerve guide or may be attached to a fiber nerve guide, suture or other solid support and used as described above for peptides. Antibody dosages are sufficient to enhance or direct neurite outgrowth, and will vary with the method of administration and the condition to be treated.

Antibodies may also be used as a "biological glue," as described above to bind multiple cadherin-expressing cells within a variety of contexts, such as to enhance wound healing and/or reduce scar tissue, and/or to facilitate cell adhesion in skin grafting or prosthetic implants. In general, the amount of matrix-linked antibody administered to a wound, graft or implant site varies with the severity of the wound and/or the nature of the wound, graft, or implant, but may vary as discussed above. Antibodies may also be linked to any of a variety of support materials, as described above, for use in tissue culture or bioreactors.

Within certain embodiments, antibodies (or, preferably, antigen-binding fragments thereof) may be used in situations where inhibition of cell adhesion is desired. Such antibodies or fragments may be used, for example, for treatment of demyelinating diseases, such as MS, or to inhibit interactions between tumor cells, as described above. The use of Fab fragments is generally preferred.

The following Examples are offered by way of illustration and not by way of limitation.

EXAMPLES

Materials and Methods

1. Phage Selection Using N-Cadherin/Fc Chimeric Protein and E-Cadherin/Fc Chimeric Protein as the Target The peptide libraries, Ph.D.-C7C™ and Ph.D.-12™ (New England BioLabs) were used in this study. These libraries are composed of $2 \times 10^9$ randomized 7 amino acid sequences flanked by cysteine residues and linear 12 amino acid sequences, respectively. The amino acid sequences are incorporated into the minor coat protein, pIII, of M13 phage. The N-cadherin/Fc chimeric protein (R&D Systems, Minneapolis, Minn.) consists of the extracellular domain of human N-cadherin (Asp160-Ala724) and the Fc region of human IgG1. The E-cadherin/Fc chimeric protein (R&D Systems, Minneapolis, Minn.) consists of the extracellular domain of human E-cadherin (Asp155-Ile707) and the Fc region of human IgG1.

Wells of a ProBind microtiter plate (Falcon) were coated with cadherin/Fc chimeric protein (1 µg/well) overnight at 4° C. To block nonspecific binding sites, TBS buffer (50 mM Tris-HCl, pH 7.4, 150 mM NaCl) containing 3% bovine serum albumin (BSA) and 1.2 mM $CaCl_2$ was added to the wells (200l/well). After 1 h incubation at 37° C., the wells were washed twice with TBST (TBS plus 0.1% Tween 20) containing 0.1% BSA and 1.2 mM $CaCl_2$. The phage ($10^{11}$ pfu) were added to each well and allowed to bind to the target protein for 1 h at room temperature with constant agitation. The unbound phage were eliminated by 10 washes with TBST containing 0.1% BSA and 1.2 mM $CaCl_2$ and the bound phage were eluted in two consecutive steps. The first elution step was performed by adding 100 µl TBS containing 2 mM EDTA to each well followed by 10 min incubation at room temperature with constant agitation. The second elution step was performed by incubating each well in 100 µl acid buffer (0.2 M glycine-HCl, pH 2.2) for 10 min at room temperature with constant agitation followed by neutralization with 1 M Tris-HCl, pH 9.1 (20 µl/well). Each fraction of eluted phage was amplified by infecting ER2738 cells and purified by polyethylene glycol (PEG) precipitation (8000 MW PEG) (Kay B. et al., 1996). The amplified phage from the EDTA fraction was used for the second round of biopanning and only the EDTA eluate was amplified and used for a third round. The amplified phage from the acid fraction was also used for a second round of biopanning and only the acid eluate was amplified for a last round. At the end of the screening, the phage were plated and isolated clones were picked randomly and amplified. The ssDNA of each phage clone was extracted using the QIAprep Spin M13 Kit (QIAGEN) according to the manufacturer's instructions. The amino acid sequences were deduced by DNA sequencing and the corresponding peptides were synthesized using Symphony®/Multiplex peptide synthesizer and Fmoc chemistry. Peptides were HPLC purified and analyzed by Mass Spectrometry.

2. Cadherin/Fc Binding Assay

The binding of each clone to the cadherin/Fc chimeric proteins was confirmed by ELISA. Wells of ProBind microtiter plates (Falcon) were coated with either N-cadherin/Fc or E-cadherin/Fc chimeric protein (100 ng/well) or human IgG1 (which contains the Fc fragment) (100 ng/well). After blocking the nonspecific sites with TBS containing 3% BSA and 1.2 mM $CaCl_2$ for 1 h at 37° C., phage clones ($10^9$ pfu) diluted in TBST containing 3% BSA and 1.2 mM $CaCl_2$ (100 µl/well). Non-coated wells were also used to exclude any phage that bound to the plastic surface. After 1 h incubation at room temperature, wells were washed 3 times with TBST containing 3% BSA and 1.2 mM $CaCl_2$. M13 phage without any insert were used to control the non-specific binding of the phage itself to the target. Monoclonal anti-M13 antibody conjugated to horseradish peroxidase (Amersham Biosciences, Piscataway, N.J.) was diluted in TBST containing 3% BSA and 1.2 mM $CaCl_2$ (1:2,000) and added to each well (100 µl/well). After 1 h incubation at room temperature, wells were washed three times with TBST containing 3% BSA and 1.2 mM $CaCl_2$ and once with TBS containing 1.2 mM $CaCl_2$.

Horseradish peroxidase substrate, TMB (Sigma), was added to each well (100 μl/well and after color development the reaction was stopped by addition of 100 μl 0.5 M sulphuric acid to each well. The intensity of the color was measured at 450 nm.

3. Evaluation of Cadherin Specificity

The phage clones shown to bind to the N-cadherin/Fc chimeric protein by ELISA were also evaluated for their ability to bind to E-cadherin/Fc and VE-cadherin/Fc chimeric proteins. The phage clones shown to bind to the E-cadherin/Fc chimeric protein by ELISA were also evaluated for their ability to bind to N-cadherin/Fc and VE-cadherin/Fc chimeric proteins. The same ELISA protocol described in the previous section was used to perform this evaluation with the exception that the wells were coated with either 100 ng N-cadherin/Fc, E-cadherin/Fc or VE-cadherin/Fc chimeric protein (R&D Systems, Minneapolis, Minn.).

4. Cell Culture

SKOV3 human ovarian cancer cells (kind gift from Dr. Riaz Farookhi, McGill University, Montreal, Quebec) were cultured in MEM containing 1.25 μg/ml Fungizone, 100 U/ml penicillin 100 μg/ml streptomycin, 0.1 mM nonessential amino acids, 2 mM L-glutamine, 10 μg/ml ml gentamicin and 10% fetal bovine serum. All culture reagents were purchased from GIBCO (Burlington, ON). To obtain confluent cell cultures, 100,000 cells per well were plated onto a 4 well slide (NalgeNunc, Naperville, Ill.) and incubated for 24 h at 37° C., in a humidified atmosphere (5% $CO_2$).

MCF-7 human breast cancer cells (kind gift from Dr. Riaz Farookhi, McGill University, Montreal, Quebec) were cultured in the same medium as SKOV3 but supplemented with 1 mM sodium pyruvate.

Human Umbilical Vein Endothelial Cells (HUVEC) and Human Dermal Microvascular Endothelial Cells (HMVEC-d) were purchased from Cambrex Bio Science Walkersville, Inc. Clonetics EGM-2 and EGM-2-MV Bulletkits (Cambrex Bio Science Walkersville, Inc) were used to culture HUVEC and HMVEC-d respectively. Cells (40,000 per well) were plated onto a 4 well slide (NalgeNunc, Naperville, Ill.) and incubated at 37° C., in a humidified atmosphere (5% $CO_2$).

Depending on their solubility, peptides were dissolved directly in culture medium and added to confluent cell cultures at the indicated concentration, or they were dissolved in dimethylformamide (DMF) to obtain a 100× concentrated solution or in water to obtain a 10× concentrated solution. The peptide stock solutions were further diluted with culture medium to a final working concentration and added to confluent cell cultures. Culture medium containing 1% solvent was used as a control. At the end of the treatment, cells were either examined by phase contrast microscopy, or fixed with 4% paraformaldehyde in PBS and stained with hematoxylin prior to light microscopic examination.

5. Surface Plasma Resonance (Biacore) Analysis

The binding of representative peptide modulating agents to either N- or VE-cadherin/Fc chimeric proteins was assessed using a BIAcore X™ Biosensor (Pharmacia Ltd., Sweden). Goat anti-human IgG recognizing N- and VE-cadherin/Fc chimeric proteins (R&D Systems, Minneapolis, Minn.) was immobilized on a CM5 sensor chip (Biacore S51) using standard amine-coupling method at 25° C. HBS-P buffer (10 mM HEPES, 0.15 M NaCl, 0.005% p20, pH 7.4) was used as the running buffer. The carboxymethyl dextran surface was activated with a 7 min injection of a 1:1 ratio of 0.4 M EDC and 0.1 M NHS. The goat anti-human IgG (Caltag Lab.) was coupled to the surface with a 7 min injection diluted in 10 mM sodium acetate, pH 5.0 to a final concentration 80 ug/ml. Remaining activated groups were blocked with a 7 min injection of 1 M ethanolamine, pH 8.5. N- and VE-cadherin/Fc chimeric proteins were dissolved in buffer containing 50 mM Tris HCl, 150 mM NaCl, and 1.2 mM $CaCl_2$ pH 7.5 to a concentration of 0.2 μM and captured on spots 1 and 2 at a flow rate of 30 μl/min for 30 min with resulting density 927 RU for N-cadherin/Fc chimeric protein and 1008 RU for VE-cadherin/Fc chimeric protein.

The linear peptide H-SWTLYTPSGQSK-$NH_2$ (SEQ ID NO: 16) and the control linear peptide H-SRTLYTPSGQSK-$NH_2$ (SEQ ID NO: 58) were passed over surfaces coated with captured N- and VE-cadherin/Fc chimeric proteins in running buffer containing 50 mM Tris-HCl, 150 mM NaCl, and 1.2 mM $CaCl_2$, pH 7.5 at concentrations ranging from 100-1.56 uM. The experiment was performed at a flow rate 90 ul/min at 25° C. Association/dissociation was observed for 1 min/2 min. All responses were referenced for reference surface and blank injections of running buffer.

Results

Identification of New N- and E-Cadherin Antagonists Using Phage Display Technology 1. Screening Against N-Cadherin/Fc Chimeric Protein To identify new N-cadherin antagonists, we screened a 7 amino acid Cys constrained library (Ph.D.-C7C™) and a 12 amino acid library (Ph.D.-12™) against a chimeric human N-cadherin containing the extracellular domain of human N-cadherin linked to the Fc portion of human IgG1 (designated as N-cadherin/Fc chimeric protein). Three rounds of biopanning resulted in a several fold phage enrichment in the EDTA eluate and in the acid eluate as described in Table 1. Phage clones selected after the third round of biopanning were mostly N-cadherin specific since more phage in the acid and EDTA eluates bound to the N-cadherin/Fc chimeric protein than to IgG1 (Table 1).

TABLE 1

Enrichment of N-cadherin/Fc chimeric protein bound phage in each eluate between the first and the third round and ratio between specific and non-specific bound phage to N-cadherin portion of the chimeric protein.

| Library | Enrichment | | N-cad/Fc bound phage/IgG1 bound phage | |
|---|---|---|---|---|
| | EDTA eluate | Acid eluate | EDTA eluate | Acid eluate |
| Ph.D.-C7C ™ | $2 \times 10^3$ | $10^5$ | $4 \times 10^3$ | $10^4$ |
| Ph.D.-C7C ™ (in the absence of calcium) | NA* | $10^2$ | NA | 10 |
| Ph.D.-12 ™ | $10^4$ | $10^5$ | $4 \times 10^4$ | $10^3$ |

*NA: not applicable

A. Screening Ph.D.-C7C™ Library

After the third round of selection with the Ph.D.-C7C™ library, 30 clones from the EDTA eluate and 10 clones from the acid eluate were randomly selected. The amino acid sequences expressed by the clones were deduced by sequencing the insert in each clone. Most of the selected clones from the EDTA eluate (27/30) and all of the selected clones from the acid eluate (10/10) bound specifically to the N-cadherin/Fc chimeric protein, as judged by ELISA. The results are summarized in Table 2.

TABLE 2

Amino Acid Sequences Expressed by Phage Clones Isolated After the Third Round of Screening the Ph.D.-C7C ™ Library Against the N-Cadherin/Fc Chimeric Protein

| Phage Clone | Amino Acid Sequence | SEQ ID NO: | Frequency Number of Clones Expressing the Amino Acid Sequence | ELISA Phage Binding to N-Cadherin/Fc Chimeric Protein 1.2 mM calcium | 2 mM EDTA | ELISA Phage Binding to Cadherin/Fc Chimeric Proteins E- | VE- |
|---|---|---|---|---|---|---|---|
| EDTA fraction | | | | | | | |
| Nc 1 | WLQPYFPSY | 32 | 19/30 | +* | –** | – | – |
| Nc 5 | WEFSICETC | 2 | 2/30 | + | – | – | – |
| Nc 8 | WTVCPIGNC | 3 | 1/30 | + | – | – | – |
| Nc 15 | WEVCLTEKC | 4 | 3/30 | + | – | – | – |
| Nc 19 | WHTSWSDTY | 33 | 1/30 | + | – | – | – |
| Nc 25 | WELCVSSSC | 5 | 1/30 | + | – | – | – |
| Acid fraction | | | | | | | |
| Nc a3 | WEVRLTEKC | 6 | 5/10 | + | – | – | – |
| Nc a5 | WLQPYFPSY | 32 | 1/10 | + | – | – | – |
| Nc a7 | WELRVSSPC | 7 | 4/10 | + | – | – | – |

*Phage bound to the chimeric protein
**No phage bound to the chimeric protein

Six different amino acid sequences were expressed by the phage from the EDTA eluate. Phage expressing these sequences bound to N-cadherin/Fc chimeric protein, and not to either epithelial (E)- or vascular endothelial (VE)-cadherin/Fc chimeric proteins, as judged by ELISA. The amino acid sequence WLQPYFPSY (SEQ ID NO: 32) was expressed by 19/30 clones and all clones expressing this sequence showed a positive ELISA signal. Furthermore, no binding to IgG1 control was detected for all clones.

The high frequency of the sequence WLQPYFPSY (SEQ ID NO: 32) suggests that it has a high affinity for N-cadherin and became, therefore, dominant in the phage population at the end of the screening process. The fact that this sequence doesn't have the two terminal Cys residues expected in the Ph.D.-C7C™ library indicates that this sequence arose from a codon bias occurring during the library preparation. This kind of clone can be isolated from a library when there is a strong selection. The 5 other sequences obtained with a lower frequency all have a N-terminal Trp residue and all showed reactivity against the N-cadherin/Fc chimeric protein, as judged by ELISA.

Three different amino acid sequences were expressed by the phage from the acid eluate. All of them had an N-terminal Trp residue and showed reactivity against the N-cadherin/Fc chimeric protein, as judged by ELISA. The sequence WEVRLTEKC (SEQ ID NO: 6) was expressed by 5/10 clones in the acid eluate and the sequence WELRVSSPC (SEQ ID NO: 7) by 4 clones. The sequence WLQPYFPSY (SEQ ID NO: 32) (previously identified in the EDTA eluate) was found only once in the acid eluate. This finding may be explained by a binding capacity that is dependent on the cadherin conformation or different affinity to its target.

An ELISA was performed in the presence of 1.2 mM calcium or 2 mM EDTA. No ELISA signal in the absence of calcium (it should be noted that calcium is essential for maintaining N-cadherin in an active conformation) was observed. These results indicate that the binding of the phage clones is dependant on the cadherin conformation and the clones being eluted by an acid buffer may be stronger binders.

The binding of the isolated Ph.D.-C7C™ phage clones to E-cadherin/Fc and VE-cadherin/Fc chimeric proteins was also evaluated by ELISA. None of the phage bound to either of these two cadherins, suggesting that they display amino acid sequences that are specific for N-cadherin.

Phage clones were also isolated from the Ph.D.-C7C™ library screened in the absence of calcium. In this experiment, three rounds of biopanning resulted in a 100-fold phage enrichment in the eluate. 90% of the eluted phage clones were N-cadherin specific and did not bind to the Fc portion of the chimeric protein. After the third round, 16 clones were randomly selected. The results are summarized in Table 3.

TABLE 3

Amino Acid Sequences Expressed by Phage Clones Isolated After the Third Round of Screening the Ph.D.-C7C ™ Library Against the N-Cadherin/Fc Chimeric Protein in the Absence of Calcium

| Phage Clone | Amino Acid Sequence | Frequency Number of Clones Expressing the Amino Acid Sequence | ELISA Phage Binding to N-Cadherin/Fc Chimeric Protein 1.2 mM Calcium | 2 mM EDTA | ELISA Phage Binding to Cadherin/Fc Chimeric Proteins E- | VE- |
|---|---|---|---|---|---|---|
| NoCa1 | WYVCVGAHC (SEQ ID NO: 8) | 13/16 | +* | + | –** | – |
| NoCa11 | WQVCVGAHC (SEQ ID NO: 9) | 1/16 | + | + | – | – |

*Phage bound to the chimeric protein
**No phage bound to the chimeric protein

Most of the selected clones bound specifically to the N-cadherin/Fc chimeric protein (14/16). Two amino acid sequences were expressed by the phage that bound to N-cadherin/Fc chimeric protein, and not to either epithelial (E)- or vascular endothelial (VE)-cadherin/Fc chimeric proteins, as judged by ELISA. It should be noted that only phage clones with a high affinity to the target will show a positive signal in the ELISA. The sequence WYVCVGAHC (SEQ ID NO: 8) was expressed by 13/16 clones and all clones expressing this sequence showed a good ELISA signal. Furthermore, no binding to IgG1 control was detected for these clones.

The high frequency of the sequence WYVCVGAHC (SEQ ID NO: 8) suggests that it has a high affinity for N-cadherin and became, therefore, dominant in the phage population at the end of the screening. The fact that this sequence doesn't have the two terminal Cys residues expected in the Ph.D.-C7C™ library indicates that this sequence arose from a codon bias occurring during the library preparation. This kind of clone can be isolated from a library when there is a strong selection. The other sequence WQVCVGAHC (SEQ ID NO: 9) obtained with a low frequency differs from the previous sequence WYVCVGAHC (SEQ ID NO: 8) by only one amino acid (a Gln residue in the second position instead of a Tyr). The phage clone expressing this amino acid sequence showed a good ELISA signal.

To evaluate whether the binding of the isolated clones to N-cadherin/Fc chimeric protein was independent of the presence of calcium, we repeated the ELISA in the presence of 1.2 mM calcium. Phage expressing the sequence WYVCVGAHC (SEQ ID NO: 8) or WQVCVGAHC (SEQ ID NO: 9) showed a strong ELISA signal independently of the presence of calcium in the buffer. These results indicate that the binding of the phage clones is independent of the cadherin conformation.

The binding of the isolated phage clones to E-cadherin/Fc and VE-cadherin/Fc chimeric proteins was also evaluated by ELISA. None of the phage bound to either of these two cadherins in the absence or presence of calcium, suggesting that they display amino acid sequences that are specific for N-cadherin.

B. Screening Ph.D.-12™ Library

The Ph.D.-12™ Library was also screened with the N-cadherin/Fc chimeric protein. After the third round, 11 clones from the EDTA eluate and 19 clones from the acid eluate were randomly selected. The amino acid sequences expressed by the clones were deduced by sequencing the insert in each clone. Most of the selected clones from the EDTA eluate (7/11) and of the selected clones from the acid eluate (18/19) bound specifically to the N-cadherin/Fc chimeric protein, as judged by ELISA. The results are summarized below in Table 4.

TABLE 4

Amino Acid Sequences Expressed by Phage Clones Isolated After the Third Round of Screening the Ph.D.-12™ Library Against the N-Cadherin/Fc Chimeric Protein

| Phage Clone | Amino Acid Sequence | SEQ ID NO: | Frequency Number of Clones Expressing the Amino Acid Sequence | ELISA Phage Binding to N-Cadherin/Fc Chimeric Protein 1.2 mM calcium | ELISA Phage Binding to N-Cadherin/Fc Chimeric Protein 2 mM EDTA | ELISA Phage Binding to Cadherin/Fc Chimeric Proteins E-   | ELISA Phage Binding to Cadherin/Fc Chimeric Proteins VE- |
|---|---|---|---|---|---|---|---|
| EDTA fraction | | | | | | | |
| Nc 12-01 | HWYITTGPVREK | 15 | 3/11 | +* | + | -** | - |
| Nc 12-04 | SWTLYTPSGQSK | 16 | 4/11 | + | - | - | - |
| Acid fraction | | | | | | | |
| Nc 12-a1 | NWFIDFPVYPPL | 17 | 7/19 | + | + | - | - |
| Nc 12-a2 | SWTLYTPSGQSK | 16 | 6/19 | + | - | - | - |
| Nc 12-a3 | KWELTYFANSFP | 18 | 1/19 | + | + | - | - |
| Nc 12-a6 | EWMIHYDSALTS | 19 | 1/19 | + | + | + | - |
| Nc 12-a7 | AWQVHYSYVASS | 20 | 2/19 | + | + | + | - |
| Nc 12-a10 | SWLAVWPATGAS | 21 | 1/19 | + | + | + | - |

*Phage bound to the chimeric protein
**No phage bound to the chimeric protein

Two different amino acid sequences were expressed by the phage from the EDTA eluate. The amino acid sequence SWTLYTPSGQSK (SEQ ID NO: 16) was expressed by 4/11 and the amino acid sequence HWYITTGPVREK (SEQ ID NO: 15) was expressed by 3/11 clones. The phage clones bearing these sequences were found to bind the N-cadherin/Fc chimeric protein, but not to either E-cadherin/Fc or VE-cadherin/Fc chimeric proteins, as judged by ELISA, suggesting that they display amino acid sequences that are specific for N-cadherin. These sequences all have a Trp residue in the second position. Furthermore, no binding to IgG1 control was detected for all clones as judged by ELISA.

Six different amino acid sequences were expressed by the phage from the acid eluate. All of them had a Trp residue in the second position and showed reactivity against the N-cadherin/Fc chimeric protein, as judged by ELISA. The sequence NWFIDFPVYPPL (SEQ ID NO: 17) was expressed by 7/19 clones. The sequence SWTLYTPSGQSK (SEQ ID NO: 16) (previously identified in the EDTA eluate) was also found (6/19 clones) in the acid eluate. Four other sequences with a Trp residue in the second position were identified in the acid eluate, but with a low frequency. The phage clones expressing these sequences bound to the N-cadherin/Fc chimeric protein with a strong signal, as judged by ELISA. Three of the phage clones also bound the E-cadherin/Fc chimeric protein, but produced a lower ELISA signal suggesting that their affinity for E-cadherin was lower than that for N-cadherin. The common feature of these 3 clones is that they all expressed a sequence with a C-terminal Ser residue. None of the clones bound to the VE-cadherin/Fc chimeric protein, as judged by ELISA.

An ELISA was performed in the presence of either 1.2 mM calcium or 2 mM EDTA. Table 4 shows that there was ELISA signal in the presence of EDTA, except for the phage clone bearing the sequence SWTLYTPSGQSK (SEQ ID NO: 16). The signal obtained in the presence of EDTA was lower than in the presence of calcium.

2. Screening Against E-Cadherin/Fc Chimeric Protein

To identify new E-cadherin antagonists, we screened a 7 amino acid Cys constrained library (Ph.D.-C7C™) and a 12 amino acid library (Ph.D.-12™) against a chimeric human E-cadherin containing the extracellular domain of human E-cadherin linked to the Fc portion of human IgG1 (designated as E-cadherin/Fc chimeric protein). Three rounds of biopanning resulted in a several fold phage enrichment in the EDTA eluate and in the acid eluate as described in Table 5.

TABLE 5

Enrichment of E-cadherin/Fc chimeric protein bound phage in each eluate between the first and third round and ratio between specific and non-specific bound phage to E-cadherin portion of the chimeric protein.

| Library | Enrichment EDTA eluate | Enrichment Acid eluate | E-cad/Fc bound phage/IgG1 bound phage EDTA eluate | E-cad/Fc bound phage/IgG1 bound phage Acid eluate |
|---|---|---|---|---|
| Ph.D.-C7C ™ | $10^3$ | $10^2$ | $5 \times 10^3$ | $10^2$ |
| Ph.D.-12 ™ | $10^4$ | $5 \times 10^2$ | $3 \times 10^2$ | $10^2$ |

A. Screening Ph.D.-C7C™ Library

After the third round, 22 clones from the EDTA eluate and 21 clones from the acid eluate were randomly selected. The amino acid sequences expressed by the clones were deduced by sequencing the insert in each clone. All of the selected clones from the EDTA eluate (22/22) and most of the selected clones from the acid eluate (20/21) bound specifically to the E-cadherin/Fc chimeric protein, as judged by ELISA. The results are summarized below in Table 6.

TABLE 6

Amino Acid Sequences Expressed by Phage Clones Isolated After the Third Round of Screening the Ph.D.-C7C ™ Library Against the E-Cadherin/Fc Chimeric Protein

| Phage clone | Amino Acid Sequence | SEQ ID NO: | Frequency Number of Clones Expressing the Amino Acid Sequence | ELISA Phage Binding to Cadherin/Fc Chimeric Proteins | | |
|---|---|---|---|---|---|---|
| | | | | E- | N- | VE- |
| EDTA fraction | | | | | | |
| Ec 7 | WTMCYPDTC | 10 | 7/22 | +* | + | -** |
| Ec 2 | WQFCYAQHC | 11 | 6/22 | + | + | - |
| Ec 4 | WQMVLCPAC | 12 | 4/22 | + | + | - |
| Ec 1 | WELVQCLTC | 13 | 4/22 | + | + | - |
| Ec 21 | WQWCFKATC | 35 | 1/22 | + | + | - |
| Acid fraction | | | | | | |
| Ec a5 | WTFNFCTAC | 14 | 15/21 | + | + | - |
| Ec a3 | WQMVLCPAC | 12 | 2/21 | + | + | - |
| Ec a22 | WTWHWPPCC | 36 | 1/21 | + | + | - |
| Ec a4 | CSKYNSPLC | 59 | 1/21 | + | + | - |
| Ec a23 | CSRPQSGLC | 60 | 1/21 | + | + | - |

*Phage bound to the chimeric protein
**No phage bound to the chimeric protein

Five different amino acid sequences were expressed by the phage from the EDTA eluate and 5 from the acid eluate. Phage expressing these sequences bound to E-cadherin/Fc and N-cadherin/Fc chimeric proteins but not to vascular endothelial (VE)-cadherin/Fc chimeric protein, as judged by ELISA. It should be noted that only phage clones with a high affinity to the target will show a positive signal in the ELISA. Furthermore, no binding to IgG1 control was detected for all clones as judged by ELISA.

The high frequency of the sequence WTFNFCTA suggests that it has a high affinity for E-cadherin and became, therefore, dominant in the phage population at the end of the screening process.

The fact that eight sequences didn't have the two terminal Cys residues expected in the C7C library indicates that these sequences arose from a codon bias occurring during the library preparation. This kind of clone can be isolated from a library when there is a strong selection. These sequences have a N-terminal Trp residue except for two sequences in the acid eluate (CSKYNSPLC (SEQ ID NO: 59) and CSRPQSGLC (SEQ ID NO: 60) and all showed reactivity against the E-cadherin/Fc and N-cadherin/Fc chimeric protein, as judged by ELISA B. Screening Ph.D.-12™ Library The Ph.D.-12 library was also screened with the E-cadherin/Fc chimeric protein. After the third round, 23 clones from the EDTA eluate and 24 clones from the acid eluate were randomly selected. The amino acid sequences expressed by the clones were deduced by sequencing the insert in each clone. Most of the selected clones from the EDTA eluate (21/23) and most of the selected clones from the acid eluate (19/24) bound to the E-cadherin/Fc chimeric protein, as judged by ELISA. The results are summarized in Table 7.

TABLE 7

Amino Acid Sequences Expressed by Phage Clones Isolated After the Third Round of Screening the Ph.D.12 ™ Library Against the E-Cadherin/Fc Chimeric Protein.

| Phage clone | Amino Acid Sequence | SEQ ID NO: | Frequency Number of Clones Expressing the Amino Acid Sequence | ELISA Phage Binding to Cadherin/Fc Chimeric Proteins | | |
|---|---|---|---|---|---|---|
| | | | | E- | N- | VE- |
| EDTA fraction | | | | | | |
| Ec 12-01 | SWTWHFPESPPP | 37 | 9/23 | +* | + | -** |
| Ec 12-06 | SWTFYWPDAQLG | 22 | 3/23 | + | + | - |
| Ec 12-07 | EWTWVFPTTHTS | 38 | 1/23 | + | + | - |
| Ec 12-10 | EWTFQWNSYPAD | 23 | 1/23 | + | + | - |
| Ec 12-19 | EWDFFWPPTQTP | 24 | 1/23 | + | + | - |
| Ec 12-22 | EWQYHWPTLQSR | 39 | 1/23 | + | + | - |
| Ec 12-11 | QWQLHWPASKQA | 25 | 2/23 | + | + | - |
| Ec 12-13 | QWTITYPKPPAL | 26 | 1/23 | + | + | - |
| Ec 12-18 | GWTVFYPDNLRP | 27 | 1/23 | + | + | - |
| Ec 12-15 | QWEWHYMAGYLA | 40 | 1/23 | + | + | - |
| Acid fraction | | | | | | |
| Ec 12-a2 | SWELYYPLRANL | 28 | 8/24 | + | + | - |
| Ec 12-a1 | QWEIRYPWPSMG | 29 | 4/24 | + | + | - |
| Ec 12-a4 | QWTYYLPLTPRW | 41 | 2/24 | + | + | - |
| Ec 12-a18 | EWTYTFPTAHSI | 42 | 2/24 | + | + | - |
| Ec 12-a13 | EWFWSWPGYSNT | 43 | 1/24 | + | + | - |
| Ec 12-a11 | SWEWYIPYLNRT | 44 | 1/24 | + | + | - |
| Ec 12-a5 | AWTWSLPTLPQS | 45 | 1/24 | + | + | - |

*Phage bound to the chimeric protein
**No phage bound to the chimeric protein

Ten different amino acid sequences were expressed by the phage from the EDTA eluate and seven from the acid eluate. Phage expressing these sequences bound to E-cadherin/Fc and N-cadherin/Fc chimeric proteins, but not to vascular endothelial (VE)-cadherin/Fc chimeric protein, as judged by ELISA. It should be noted that only phage clones with a high affinity to the target will show a positive signal in the ELISA. Furthermore, no binding to IgG1 control was detected for all clones, as judged by ELISA. These sequences all have a Trp residue in the second position.

3. Biological Activities of Illustrative Peptides

Several linear peptides were synthesized having amino acid sequences identical to those displayed by the N-cadherin/Fc chimeric protein-specific phage clones, as well as control peptides, as follows: H-WELRVSSP-NH$_2$ (SEQ ID NO: 47) and the control peptide H-AELRVSSP-NH$_2$ (SEQ ID NO: 61); H-WYVCVGAH-NH$_2$ (SEQ ID NO: 46) and the control peptide H-RYVCVGAH-NH$_2$ (SEQ ID NO: 62); H-HWYITTGPVREK-NH$_2$ (SEQ ID NO: 15), H-SWT-LYTPSGQSK-NH$_2$ (SEQ ID NO: 16) and the control peptide H-SRTLYTPSGQSK-NH$_2$ (SEQ ID NO: 58) These peptides were analyzed for their ability to disrupt SKOV3 human ovarian cancer cell adhesion. Confluent cultures of SKOV3 cells were incubated in the presence of individual peptides.

Confluent SKOV3 cultures were incubated in the presence of the linear peptide H-WYVCVGAH-NH$_2$ (SEQ ID NO: 46) at various concentrations (50, 100 and 150 µg/ml medium) for 24 h. This peptide was capable of disrupting cell adhesion and altering cell morphology at concentrations of 100 and 150 µg/ml. The effect of H-WYVCVGAH-NH$_2$ (SEQ ID NO: 46) on SKOV3 cell adhesion was evident after 9 h culture, and more pronounced after 24 h. In contrast, the control peptide H-RYVCVGAH-NH$_2$ (SEQ ID NO: 62) (the terminal Trp residue being replaced with an Arg residue) had no effect on cell adhesion. These observations demonstrate the importance of the Trp residue for H-WYVCVGAH-NH$_2$ (SEQ ID NO: 46) biological activity.

The ability of H-WYVCVGAH-NH$_2$ (SEQ ID NO: 46) (at a concentration of 100 μg/ml) to disrupt MCF-7 cell adhesion was also evaluated. These cells express E-cadherin, but not N-cadherin. The peptide did not affect MCF-7 cell adhesion. These results are consistent with the peptide H-WYVCVGAH-NH$_2$ (SEQ ID NO: 46) representing an N-cadherin-specific antagonist.

Peptides H-SWTLYTPSGQSK-NH$_2$ (SEQ ID NO: 16) and H-HWYITTGPVREK-NH$_2$ (SEQ ID NO: 15) were tested for their ability to disrupt HUVEC and HMVEC adhesion. Human endothelial cells express N- and VE-cadherin. Confluent cultures were incubated in the presence of the peptides (1 mg/ml medium) for various periods of time. The linear peptide H-SWTLYTPSGQSK-NH$_2$ (SEQ ID NO: 16) disrupted HUVEC adhesion after 5 min of incubation, with a maximum effect at 1 h. In contrast, the peptide H-HWYITTGPVREK-NH$_2$ (SEQ ID NO: 15) had no effect on HUVEC adhesion after 1 h incubation. The effect of H-SWTLYTPSGQSK-NH$_2$ (SEQ ID NO: 16) on HUVEC adhesion was dose-dependent. After 1 h incubation, this peptide disrupted cell adhesion at concentrations of 0.125 mg/ml and higher. A moderate activity was observed at a peptide concentration of 0.062 mg/ml. The control peptide H-SRTLYTPSGQSK-NH$_2$ (SEQ ID NO: 58) had no biological activity at the highest concentration of 1 mg/ml. Collectively, these results indicate that the Trp residue is important for the activity of the peptide H-SWTLYTPSGQSK-NH$_2$, (SEQ ID NO: 16) but also that the amino acids surrounding the Trp residue affect the activity.

The peptide H-SWTLYTPSGQSK-NH$_2$ (SEQ ID NO: 16) was also capable of disrupting HMVEC adhesion in a dose-dependent manner. Cell adhesion was disrupted at a peptide concentration of 0.062 mg/ml, with more pronounced effects being observed at 0.125 mg/ml, and still stronger effects occurring at peptide concentrations of 0.5 mg/ml and higher. The control peptide H-SRTLYTPSGQSK-NH$_2$ (SEQ ID NO: 58) had no biological activity at the highest concentration of 1 mg/ml. The peptide H-SWTLYTPSGQSK-NH$_2$ (SEQ ID NO: 16) also disrupted SKOV3 cell adhesion (these cells express N-cadherin), whereas the control peptide H-SRTLYTPSGQSK-NH$_2$ (SEQ ID NO: 58) had no effect.

The ability of H-SWTLYTPSGQSK-NH$_2$ (SEQ ID NO: 16) to disrupt MCF-7 cell adhesion (these cells express E-cadherin) was evaluated. This peptide did not affect MCF-7 cell adhesion. These results support the contention that H-SWTLYTPSGQSK-NH$_2$ (SEQ ID NO: 16) is an N-cadherin-specific antagonist.

The PEGylated peptide H-SWTLYTPSGQSK-(succinyl-PEG$_{5000}$-OMe)—NH$_2$ (SEQ ID NO: 63) (4.7 mg/ml) also showed a strong activity on HUVEC adhesion. Cell adhesion was disrupted within one hour incubation.

The ability of the peptides H-EWMIHYDSALTS-NH$_2$ (SEQ ID NO: 19) and H-SWELYYPLRANL-NH$_2$ (SEQ ID NO: 28) to disrupt SKOV3 and MCF7 cell adhesion was examined. The linear peptides H-EWMIHYDSALTS-NH$_2$ (SEQ ID NO: 19) and H-SWELYYPLRANL-NH$_2$ (SEQ ID NO: 28) (1 mg/ml) disrupted MCF-7 and SKOV3 cell adhesion.

The peptide H-WELRVSSP-NH$_2$ (SEQ ID NO: 47) was also found to be biologically active. This linear peptide was capable of disrupting cell adhesion and altering cell morphology at the concentration of 0.5 mg/ml. In contrast, the control peptide H-AELRVSSP-NH$_2$ (SEQ ID NO: 61) that had its terminal Trp residue replaced with an Ala residue had no biological activity. These observations demonstrate the importance of the Trp residue for biological activity. The results of these studies are summarized below in Table 8.

TABLE 8

Summary of the Biological Activities of Illustrative Peptides

| Amino Acid Sequence of Peptide | Peptide Binds to | | Peptide Disrupts Adhesion of | | | |
|---|---|---|---|---|---|---|
| | N-cad/Fc* | E-cad/Fc** | SKOV3 cells | MCF-7 cells | HUVEC | HMVEC |
| H-WYVCVGAH-NH$_2$ (SEQ ID NO: 46) | +# | -## | + | - | nd | nd |
| H-RYVCVGAH-NH$_2$ (SEQ ID NO: 62) | nd@ | nd | - | nd | nd | nd |
| H-HWYITTGPVREK-NH$_2$ (SEQ ID NO: 15) | + | - | nd | nd | - | nd |
| H-SWTLYTPSGQSK-NH$_2$ (SEQ ID NO: 16) | + | - | + | - | + | + |
| H-SRTLYTPSGQSK-NH$_2$ (SEQ ID NO: 58) | - | nd | - | nd | - | - |
| H-EWMIHYDSALTS-NH$_2$ (SEQ ID NO: 19) | + | + | + | + | nd | nd |
| H-SWELYYPLRANL-NH$_2$ (SEQ ID NO: 28) | + | + | + | + | nd | nd |
| H-WELRVSSP-NH$_2$ (SEQ ID NO: 47) | + | - | + | nd | nd | nd |

TABLE 8-continued

Summary of the Biological Activities of Illustrative Peptides

| Amino Acid Sequence of Peptide | Peptide Binds to | | Peptide Disrupts Adhesion of | | | |
|---|---|---|---|---|---|---|
| | N-cad/ Fc* | E-cad/ Fc** | SKOV3 cells | MCF-7 cells | HUVEC | HMVEC |
| H-AELRVSSP-NH₂ (SEQ ID NO: 61) | nd | nd | – | nd | nd | nd |

*human N-cadherin/Fc chimeric protein
**human E-cadherin/Fc chimeric protein
yes
no
@not determined 4. Surface Plasma Resonance (Biacore) Analysis The binding of the linear peptide H-SWTLYTPSGQSK-NH₂ (SEQ ID NO: 16) to N- and VE-cadherin/Fc chimeric proteins was analyzed by surface plasma resonance. The linear peptide H-SWTLYTPSGQSK-NH₂ (SEQ ID NO: 16) bound to the N-cadherin/Fc chimeric protein with an affinity of 66 μM. This peptide did not bind to the VE-cadherin/Fc chimeric protein. The control linear peptide H—SRTLYTPS-GQSK-NH₂ (SEQ ID NO: 58) did not bind to either N-cadherin/Fc or VE-cadherin/Fc chimeric proteins. The kinetic parameters for the interaction of the linear peptide H-SWTLYTPSGQSK-NH₂ (SEQ ID NO: 16) with the N-cadherin/Fc chimeric protein surface are: $k_a=6.1(2)\times10^3$ $M^{-1}s^{-1}$, $k_d=0.407(8)$ $s^{-1}$ and $K_D=6.6(2)\times10^{-5}$ M. These results confirm the importance of the Trp residue for H-SWTLYTPS-GQSK-NH₂ (SEQ ID NO: 16) binding to N-cadherin.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A cell adhesion modulating agent that modulates a cadherin-mediated process, wherein the agent comprises a peptide selected from the group consisting of WEFSICETC (SEQ ID NO: 2), WTVCPIGNC (SEQ ID NO: 3), WEVCLTEKC (SEQ ID NO: 4), WELCVSSSC (SEQ ID NO: 5), WEVRLTEKC (SEQ ID NO: 6), WELRVSSPC (SEQ ID NO: 7), WYVCVGAHC (SEQ ID NO: 8), WQVCVGAHC (SEQ ID NO: 9), WTMCYPDTC (SEQ ID NO: 10), WQFCYAQHC (SEQ ID NO: 11), WQMVLCPAC (SEQ ID NO: 12), WELVQCLTC (SEQ ID NO: 13), WTFNFCTAC (SEQ ID NO: 14), HWYITTGPVREK (SEQ ID NO: 15), SWTLYTPSGQSK (SEQ ID NO: 16), NWFIDFPVYPPL (SEQ ID NO: 17), KWELTYFANSFP (SEQ ID NO: 18), EWMIHYDSALTS (SEQ ID NO: 19), AWQVHYSYVASS (SEQ ID NO: 20), SWLAVWPATGAS (SEQ ID NO: 21), SWTFYWPDAQLG (SEQ ID NO: 22), EWTFQWNSYPAD (SEQ ID NO: 23), EWDFFWPPTQTP (SEQ ID NO: 24), QWQLHWPASKQA (SEQ ID NO: 25), QWTITYPKPPAL (SEQ ID NO: 26), GWTVFYPDNLRP (SEQ ID NO: 27), SWELYYPLRANL (SEQ ID NO: 28), and QWEIRYPWPSMG (SEQ ID NO: 29).

2. A cell adhesion modulating agent that modulates a cadherin-mediated process, wherein the agent comprises a peptide sequence selected from the group consisting of WEFSICETC (SEQ ID NO: 2), WEVCLTEKC (SEQ ID NO: 4), WELCVSSSC (SEQ ID NO: 5), WEVRLTEKC (SEQ ID NO: 6) and WELRVSSPC (SEQ ID NO: 7).

3. A cell adhesion modulating agent that modulates a cadherin-mediated process and comprises a CAR sequence having the following formula:

W-L/H-Q/T-P/S-Y/W-F/S-P/D-S/T-Y  (SEQ ID NO: 31)

wherein L/H is Leu or His, Q/T is Gln or Thr, P/S is Pro or Ser, Y/W is Tyr or Trp, F/S is Phe or Ser, P/D is Pro or Asp, and S/T is Ser or Thr.

4. A cell adhesion modulating agent that modulates a cadherin-mediated process wherein the agent comprises a peptide sequence selected from the group consisting of WLQPYFPSY (SEQ ID NO: 32) and WHTSWSDTY (SEQ ID NO: 33).

5. A cell adhesion modulating agent that modulates a cadherin-mediated process and comprises a CAR sequence having the following formula:

W-Y/Q-VCVGAH  (SEQ ID NO: 34)

wherein Y/Q is Tyr or Gln.

6. The cell adhesion modulating agent according to claim 5 wherein the agent comprises a peptide sequence selected from the group consisting of WYVCVGAHC (SEQ ID NO: 8) and WQVCVGAHC (SEQ ID NO: 9).

7. A cell adhesion modulating agent that modulates a cadherin-mediated process and comprises one or more peptide sequences selected from the group consisting of WTMCYPDTC (SEQ ID NO: 10), WQFCYAQHC (SEQ ID NO: 11), WQMVLCPAC (SEQ ID NO: 12), WELVQCLTC (SEQ ID NO: 13), WQWCFKATC (SEQ ID NO: 35), WTFNFCTAC (SEQ ID NO: 14), WTWHWPPCC (SEQ ID NO: 36), HWYITTGPVREK (SEQ ID NO: 15), SWTLYTPSGQSK (SEQ ID NO: 16), NWFIDFPVYPPL (SEQ ID NO: 17), KWELTYFANSFP (SEQ ID NO: 18), EWMIHYDSALTS (SEQ ID NO: 19), AWQVHYSYVASS (SEQ ID NO: 20), SWLAVWPATGAS (SEQ ID NO: 21), SWTWHFPESPPP (SEQ ID NO: 37), SWTFYWPDAQLG (SEQ ID NO: 22), EWTWVFPTTHTS (SEQ ID NO: 38), EWTFQWNSYPAD (SEQ ID NO: 23), EWDFFWPPTQTP (SEQ ID NO: 24), EWQYHWPTLQSR (SEQ ID NO: 39), QWQLHWPASKQA (SEQ ID NO: 25), QWTITYPKPPAL (SEQ ID NO: 26), GWTVFYPDNLRP (SEQ ID NO: 27), QWEWHYMAGYLA (SEQ ID NO: 40), SWELYYPLRANL (SEQ ID NO: 28), QWEIRYPWPSMG (SEQ ID NO: 29), QWTYYLPLTPRW (SEQ ID NO: 41), EWTYTFPTAHSI (SEQ ID NO: 42), EWFWSWPGYSNT (SEQ ID NO: 43), SWEWYIPYLNRT (SEQ ID NO: 44) and AWTWSLPTLPQS (SEQ ID NO: 45).

8. A cell adhesion modulating agent that modulates a cadherin-mediated process and comprises one or more CAR sequences selected from the group consisting of WYVCVGAH (SEQ ID NO: 46), HWYITTGPVREK (SEQ ID NO: 15), SWTLYTPSGQSK (SEQ ID NO: 16), EWMIHYDSALTS (SEQ ID NO: 19), SWELYYPLRANL (SEQ ID NO: 28), and WELRVSSP (SEQ ID NO: 47).

9. A method for modulating cell adhesion comprising contacting a cell that expresses a classical cadherin with a cell adhesion modulating agent of any one of claim 3, 5, 7, or 8 and thereby modulating cell adhesion.

10. A cell adhesion modulating agent that modulates a cadherin-mediated process and comprises the peptide sequence SWELYYPLRANL (SEQ ID NO: 28).

11. The cell adhesion modulating agent of claim 10, wherein the agent is adapted for transdermal administration.

* * * * *